US012594135B2

(12) United States Patent
Gaither et al.

(10) Patent No.: US 12,594,135 B2
(45) Date of Patent: Apr. 7, 2026

(54) NETWORK VIRTUALIZATION FOR REMOTELY CONTROLLING ROBOTIC-ASSISTED MEDICAL PROCEDURES

(71) Applicant: Sovato Health, Inc., Goleta, CA (US)

(72) Inventors: Brian Gaither, South Weber, UT (US); Daniel Wayne Haskell, Santa Barbara, CA (US); Cynthia Perazzo, Huntington Beach, CA (US); Tyler Grotenhuis, Santa Barbara, CA (US); Blair Whitney, Santa Barbara, CA (US)

(73) Assignee: Sovato Health, Inc., Goleta, CA (US)

( * ) Notice: Subject to any disclaimer, the term of this patent is extended or adjusted under 35 U.S.C. 154(b) by 0 days.

(21) Appl. No.: 19/320,605

(22) Filed: Sep. 5, 2025

(65) Prior Publication Data

US 2026/0020924 A1     Jan. 22, 2026

Related U.S. Application Data

(63) Continuation-in-part of application No. 19/273,545, filed on Jul. 18, 2025, which is a continuation-in-part of application No. 19/191,839, filed on Apr. 28, 2025.

(60) Provisional application No. 63/855,211, filed on Jul. 31, 2025, provisional application No. 63/741,379, filed on Jan. 2, 2025, provisional application No. 63/674,187, filed on Jul. 22, 2024.

(51) Int. Cl.
*A61B 34/30* (2016.01)

(52) U.S. Cl.
CPC .................................. *A61B 34/30* (2016.02)

(58) Field of Classification Search
CPC ....................................................... A61B 34/30
USPC .......................................................... 700/245
See application file for complete search history.

(56) References Cited

U.S. PATENT DOCUMENTS

| | | | |
|---|---|---|---|
| 7,222,000 B2 | 5/2007 | Wang et al. |
| 7,289,883 B2 | 10/2007 | Wang et al. |
| 7,292,912 B2 | 11/2007 | Wang et al. |
| 7,761,185 B2 | 7/2010 | Wang et al. |
| 8,209,051 B2 | 6/2012 | Wang et al. |
| 8,340,819 B2 | 12/2012 | Mangaser et al. |
| 8,463,435 B2 | 6/2013 | Herzog et al. |
| 8,836,751 B2 | 9/2014 | Ballantyne et al. |
| 8,849,680 B2 | 9/2014 | Wright et al. |
| 9,138,891 B2 | 9/2015 | Herzog et al. |
| 9,160,783 B2 | 10/2015 | Pinter |

(Continued)

OTHER PUBLICATIONS

Ahmed, et al. Implementing Data center Overlay Protocols, Cisco Press (2020), in 38 pages.

(Continued)

*Primary Examiner* — Kira Nguyen
(74) *Attorney, Agent, or Firm* — Knobbe, Martens, Olson & Bear, LLP

(57) ABSTRACT

Disclosed systems, apparatuses, and methods enable remotely controlling robotic-assisted medical systems, such as robotic-assisted surgery systems, for performing remote robotic-assisted medical procedures. Disclosed approaches provide a secure, efficient, and dynamically-created virtual network for connecting physician consoles and robotic-assisted medical systems. Disclosed approaches improve efficiency, security, scalability, and reliability of remote robotic-assisted medical procedures.

23 Claims, 11 Drawing Sheets

(56) References Cited

U.S. PATENT DOCUMENTS

| | | | |
|---|---|---|---|
| 9,198,728 B2 | 12/2015 | Wang et al. | |
| 9,251,313 B2 | 2/2016 | Ross et al. | |
| 9,264,664 B2 | 2/2016 | Pinter et al. | |
| 9,375,843 B2 | 6/2016 | Wang et al. | |
| 9,842,192 B2 | 12/2017 | Wang et al. | |
| 9,849,593 B2 | 12/2017 | Wang et al. | |
| 10,924,708 B2 | 2/2021 | Pinter et al. | |
| 11,154,981 B2 | 10/2021 | Hanrahan et al. | |
| 11,636,944 B2 | 4/2023 | Hanrahan et al. | |
| 11,812,924 B2* | 11/2023 | Garcia Kilroy | A61B 34/37 |
| 12,042,239 B1 | 7/2024 | Whitney et al. | |
| 12,089,906 B1 | 9/2024 | Whitney et al. | |
| 2005/0204438 A1 | 9/2005 | Wang et al. | |
| 2006/0047821 A1 | 3/2006 | Kim | |
| 2008/0201017 A1 | 8/2008 | Wang et al. | |
| 2011/0071702 A1 | 3/2011 | Wang et al. | |
| 2018/0250086 A1 | 9/2018 | Grubbs | |
| 2018/0338806 A1* | 11/2018 | Grubbs | A61B 34/30 |
| 2020/0197116 A1* | 6/2020 | Linebarger | A61B 18/1482 |
| 2020/0405417 A1* | 12/2020 | Shelton, IV | A61B 90/361 |
| 2021/0007814 A1* | 1/2021 | Shuma | A61B 34/74 |
| 2021/0220064 A1 | 7/2021 | Kottenstette et al. | |
| 2023/0128665 A1 | 4/2023 | Kottenstette et al. | |
| 2024/0099792 A1* | 3/2024 | Kitatsuji | A61B 90/361 |

OTHER PUBLICATIONS

Ghodoussi et al., "Robotic Surgery—The Transatlantic Case", Proceedings of the 2002 IEEE International Conference on Robotics & Automation, Washington, DC, May 2002, pp. 1882-1888.

Gu et al., "Robotic surgery in China", The Innovation, Sep. 11, 2023, vol. 4, No. 5, in 2 pages.

Teladoc Health, Teladoc HealthTM Care Location App ModuleTM User Guide, 2021, in 71 pages.

Teladoc Health, "Teladoc HealthTM Lite V2 & V3 Under Guide", 2021, in 65 pages.

Edge Medical, Tele-Surgery System—Edge Medical World Leading and Fast-Growing Surgical Robot Company (2023), in 2 pages.

Crusco, et al., Comparing the da Vinci Si Single Console and Dual Console in Teaching Novice Surgeons Suturing Techniques, JSLS 18(3):1-6 (2014).

* cited by examiner

600

NETWORK VIRTUALIZATION FOR REMOTELY CONTROLLING ROBOTIC-ASSISTED MEDICAL PROCEDURES

CROSS-REFERENCE TO RELATED APPLICATIONS

This application claims priority to U.S. Provisional Patent Application No. 63/855,211, filed on Jul. 31, 2025, which is incorporated by reference in its entirety. This application is a continuation in part of U.S. patent application Ser. No. 19/273,545, filed on Jul. 18, 2025, which is a continuation in part of U.S. patent application Ser. No. 19/191,839, filed on Apr. 28, 2025, which claims priority to U.S. Provisional Patent Application No. 63/674,187 filed on Jul. 22, 2024 and U.S. Provisional Patent Application No. 63/741,379 filed on Jan. 2, 2025, each of which is incorporated by reference in its entirety.

TECHNICAL FIELD

This disclosure relates generally to approaches for network virtualization for connecting physicians to robotic medical procedure systems to perform remote robotic-assisted medical procedures.

DESCRIPTION OF RELATED ART

Robot-assisted surgery systems are generally available and have been developed to operate efficiently and safely. A robotic surgery system typically includes robotically actuable surgical instruments that may be inserted within the patient's body to perform a surgical procedure at a physician site. The robotic surgery system is typically controlled by a physician via a physician input console, which is connected to the robotic surgery system via a control cable. The physician input console includes input devices that are grasped by the physician's hands and moved to generate signals for activating the surgical instruments to perform surgical operations at the surgical site. Signals are transmitted over the control cable to the robotic surgery system, which interprets the signals and generates control signals that cause the instruments to be actuated to perform surgical operations.

SUMMARY

Disclosed systems, apparatuses, and methods enable remotely controlling robotic-assisted medical systems, such as robotic-assisted surgery systems, via network virtualization. Such disclosed approaches provide a scalable, flexible, and efficient network for connecting remote physician consoles and robotic-assisted medical procedure systems. Disclosed approaches improve efficiency, safety, and availability of robotic-assisted medical procedures (also referred to as robotic-assisted procedures or robotic procedures).

For physicians or other medical professionals, advantageously, remote procedures facilitate optimal utilization of their time and provide access to a sufficient volume of patients to perfect their skills. For patients, advantageously, remote procedures create ample access to the right physician or medical professional and the right care at an affordable price, decreases the need for travel, and reduces delayed care. Network virtualization facilitates scalability, security, and ease of deployment for performing robotic-assisted medical procedures remotely. Disclosed approaches facilitate patient safety and increase the effectiveness and security of remotely controlled robotic procedures.

Other aspects and features will become apparent to those ordinarily skilled in the art upon review of the following description of specific disclosed implementations in conjunction with the accompanying figures.

BRIEF DESCRIPTION OF THE DRAWINGS

Specific implementations will now be described with reference to the following drawings, which are provided by way of example.

DETAILED DESCRIPTION

Figure 1:
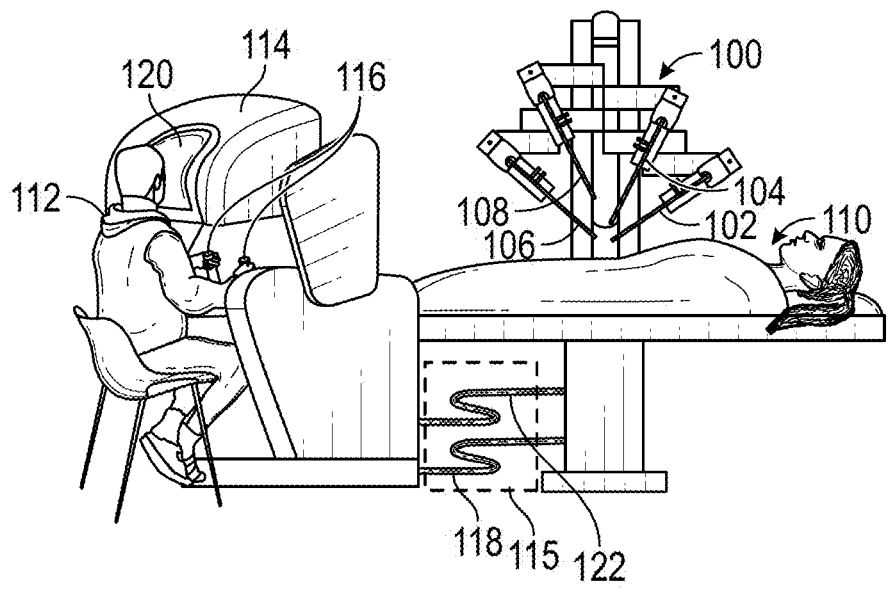
FIG. 1 is perspective view of a robotic surgery system.

Referring to FIG. 1, a robotic medical procedure system, in particular, a robotic surgery system is shown generally at 100. The robotic surgery system 100 includes a plurality of robotically actuable surgical instruments 102-108 positioned on one or more robotic arms. At least one of the instruments 102-108 will generally be configured as an in-patient imaging system (such as, a camera, fluoroscopy system which can obtain a continuous X-ray image, radiography system, computer tomography (CT) system, ultrasound system, magnetic resonance imaging (MRI) system, or the like), which may be inserted into the body of the patient to generate images of anatomical structures and the surgical instruments 102-108 at a surgical site within the body of a patient 110. In some instances, a plurality of imaging systems can be utilized by the robotic surgery system 100. In some cases, one or more imaging systems may not need to be inserted into the patient's body. The remaining instruments may be configured to include an end effector that performs a specific surgical function (such as, forceps/graspers, needle drivers, scissors, electrocautery hooks, staplers, clip appliers, removers, etc.). The system 100 is controlled by a surgeon 112 via a surgeon input console 114, which is connected to the robotic surgery system 100 via a control cable 118. The surgeon input console 114 includes input devices (not shown) including handles 116 that are grasped by the surgeon's left and right hands and moved within an input device workspace or otherwise actuated to generate input signals. The input devices include encoders that transform positions and orientations of the handles 116 into input signal data representing the surgeon input. The input signals may thus be used for activating the plurality of surgical instruments 102-108 to perform surgical operations at the surgical site. The input signals are transmitted over the control cable 118 to the system 100, which interprets the signals and generates control signals that cause the instruments 102-108 to be actuated to move and perform other surgical operations. The input signals will generally be output by the input devices on the surgeon input console 114 as data signals representing the inputs to the console provided by the surgeon 112. For example, the surgeon input console 114 may generate input signals in the form of motion control signals that represent instantaneous positions of the handles 116 of the input devices within an input device workspace. The data signals are transmitted over the control cable 118, which is generally a wired connection between the surgeon input console 114 and the robotic surgery system 100. The wired connection ensures negligible transmission delay such that operations of the surgical instruments 102-108 caused by the surgeon will be effected by the system 100 with negligible delay. Transmission over the control cable 118 may be implemented using any of a variety of different data transmission technologies such as Ethernet or Controller Area Network (CAN bus) protocol.

The robotic surgery system 100 can include a patient cart that supports the robotic arms. In some instances, a separate vision cart that supports one or more imaging systems can be included. The robotic surgery system 100 can also include a tower that serves as a central hub to which the patient cart and vision cart (if present) are connected. Any network connections to the robotic surgery system described herein can be made to the tower.

Additional input signals may also be generated at the surgeon input console 114. For example, the handles 116 may include other controls (not shown) that may be used to generate actuation signals that actuate operations at the surgical instruments 102-108, such as opening or closing a surgical scissor or forceps. The surgeon input console 114 may also include one or more foot pedals (not shown) that may be actuated by the surgeon to initiate various other operations. For example, a foot pedal may be configured to generate a clutch signal for temporarily decoupling the surgical instruments 102-108. A foot pedal may also be configured to initiate delivery of energy, such as generate electrocautery signals for initiating delivery of an electro-cauterization current to an instrument, to cut, cauterize, or coagulate tissue (which can involve resection of tissue, vaporization of tissue, or coagulation of tissue). Delivery of energy can include delivery of ultrasonic energy (such as, with a harmonic scalpel instrument), delivery of electric energy (such as, with an electrocautery instrument), delivery of laser energy (such as, with a cautery instrument), delivery of radio frequency energy (such as, with a cautery instrument), or the like. These other input signals also need to be delivered to the robotic surgery system 100 to initiate their respective operations. Additionally, the robotic surgery system 100 may generate event-oriented notifications such as notifications of error conditions that must be communicated to the physician input console 114 to update the physician 112. Event-oriented messages may be time-sensitive, but are not necessarily synchronous.

The physician input console 114 also includes a display 120 for displaying images generated by the in-patient imaging system. The in-patient imaging system would generally be implemented as a high-resolution imaging system (such as, a video camera) that generates a stream of image frames. In some instances, the imaging system may generate images from differing perspectives that convey three-dimensional information and the display 120 may be configured as a stereoscopic display. The display signals generated by the imaging system are transmitted over an image transmission cable 122 back to the physician input console 114 for driving the display 120. The image transmission cable 122 is generally selected to ensure that the image frames are delivered to the display in near real-time so that the physician 112 does not perceive any delay between their hand movements and movements of the surgical instruments 102-108 represented on the display. In some implementations, the input signals and display signals may both be transmitted over a single shared cable or bus.

A connection 115 can be used for transmission of data between the robotic surgery system 100 and the surgeon input console 114. As illustrated in FIG. 1, the connection 115 can utilize the control cable 118 and the image transmission cable 122. The connection 115 can be a direct connection that links the robotic surgery system 100 and the surgeon input console 114. The connection 115 can be isolated from any other network. For instance, the connection 115 can be a direct local area network (LAN) connection.

The robotic surgery system 100 may be housed within a sterile operating room that forms part of an operating suite. The surgeon or another surgeon aided by a perioperative nurse may make the necessary incisions and insert the instruments 102-108. The surgeon input console 114 may be housed in a portion of the operating suite that is separated from the operating room so that the surgeon operating the input console need not wear surgical gloves while manipulating the controls of the input console. The cables 118 and 122 would generally extend through a port in a wall between the surgeon input console 114 and the robotic surgery system 100. In cases where another surgeon performs the incisions in the body of the patient 110, the operating surgeon may not need to complete the full process of scrubbing, gowning, and gloving before the operation. In this situation, the surgeon input console 114 however remains in a direct wired connection with the robotic surgery system 100 via the cables 118 and 122. The direct wired connection ensures that the robotic surgery system 100 is able to rapidly respond to the surgeon's inputs provided at the surgeon input console 114 and the display 120 displays images of the surgical site with a negligible delay that is virtually unnoticeable to the surgeon.

Overview of Remotely Controlling Robotic Procedures

While certain examples are described in the context of remotely controlling a surgical procedure performed by a robotic surgery system, the approaches described herein can be used for remotely controlling a variety of medical procedures, including invasive and non-invasive procedures as well as surgical and non-surgical procedures. The approaches described herein can be used for remotely controlling surgical procedures, interventional procedures, or diagnostic procedures (such as, procedures not involving manipulation of tissue). Medical procedures can be performed by patient-side robotic procedure systems that are controlled by physician-side robotic procedure consoles. Patient-side robotic procedure systems can have one of more features of the robotic surgery systems described herein, such as one or more of an imaging system on a robotic arm or an instrument on a robotic arm. Physician-side robotic procedure consoles described herein can have one or more features of the input consoles described herein, such as one or more displays and input devices.

One of the main problems in the healthcare industry is the lack of physicians (for instance, surgeons) and their under-utilization. On one hand, there is a lack of high-quality physicians. For instance, a 2022 article by the American College of Surgeons concludes that there is an acute ongoing shortage of surgeons available in the United States to serve the patient population. The shortage of high-quality surgical care is particularly severe in rural areas. In addition, surgeons in many geographical areas may not have access to a sufficient volume of patients to perfect their surgical skills because the population is not evenly distributed, thus creating a lack of surgical volume in such areas. On the other hand, currently there are severe inefficiencies with utilizing the time of physicians. For instance, surgeons are required to travel between different hospitals, some of which may be located in difficult to reach places or between different operating rooms in a single hospital. Moreover, surgeons are required to wait for patients and operating rooms to be prepared for surgery. This results in a serious underutilization of surgeons' time. There are many advantages in allowing surgeons to control robotic surgery systems (such as, the system 100) from remote locations in order to increase efficiency and improve patient care. For surgeons, remote surgery facilitates optimal utilization of their time and provides access to a sufficient volume of patients to perfect their skills. For patients, remote surgery creates ample access to the right surgeon and the right care at an affordable price, decreases the need for travel, and decreases delayed care. However, there are a number of challenges with designing a system that would allow remotely controlling robotic surgery systems. These include transmission delay, availability, and reliability of transmission.

Figure 2:
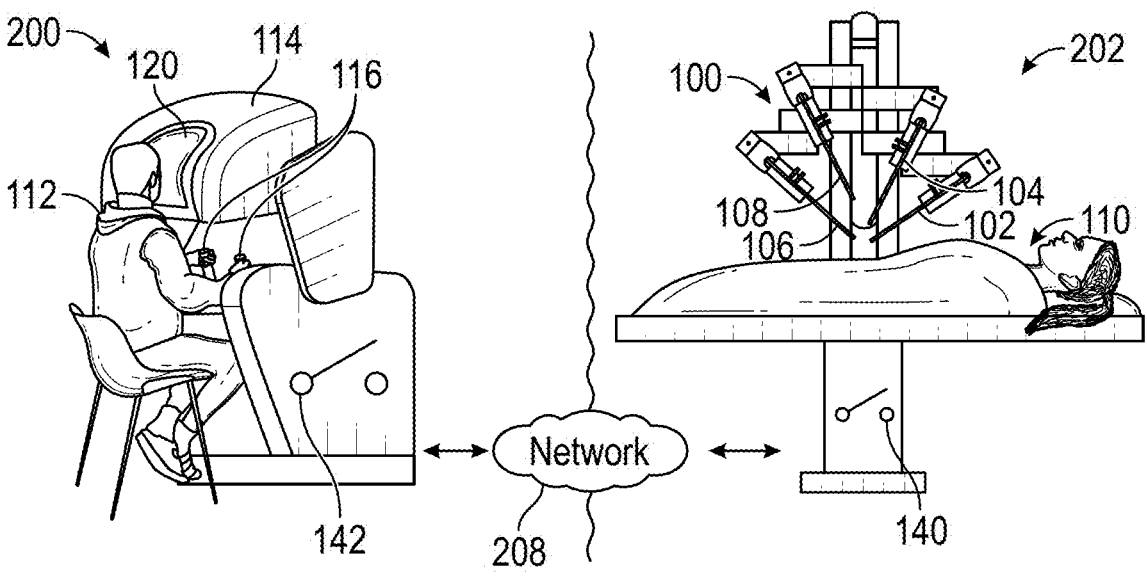
FIG. 2 is perspective view of a robotic surgery system.

Referring to FIG. 2, the surgeon input console 114 is disposed at a surgeon-side location 200 and the robotic surgery system 100 shown in FIG. 1 is disposed at a patient-side location 202. The surgeon-side location 200 is remote from the patient-side location 202 to an extent where a directly wired connection between the robotic surgery system 100 and the surgeon input console 114 is no longer possible. Advantageously, the surgeon-side location 200 may be in another building or even another city, state, or country. In this example, communication is performed between the surgeon-side location 200 and the patient-side location 202 via a network 208, and there is no direct connection 115 between the surgeon input console 114 and the robotic surgery system 100.

The robotic surgery system 100 can include a switching circuitry 140, and the surgeon input console 114 can include switching circuitry 142. The operation of the switching circuitries 140 and 142 is explained below.

Figure 3:
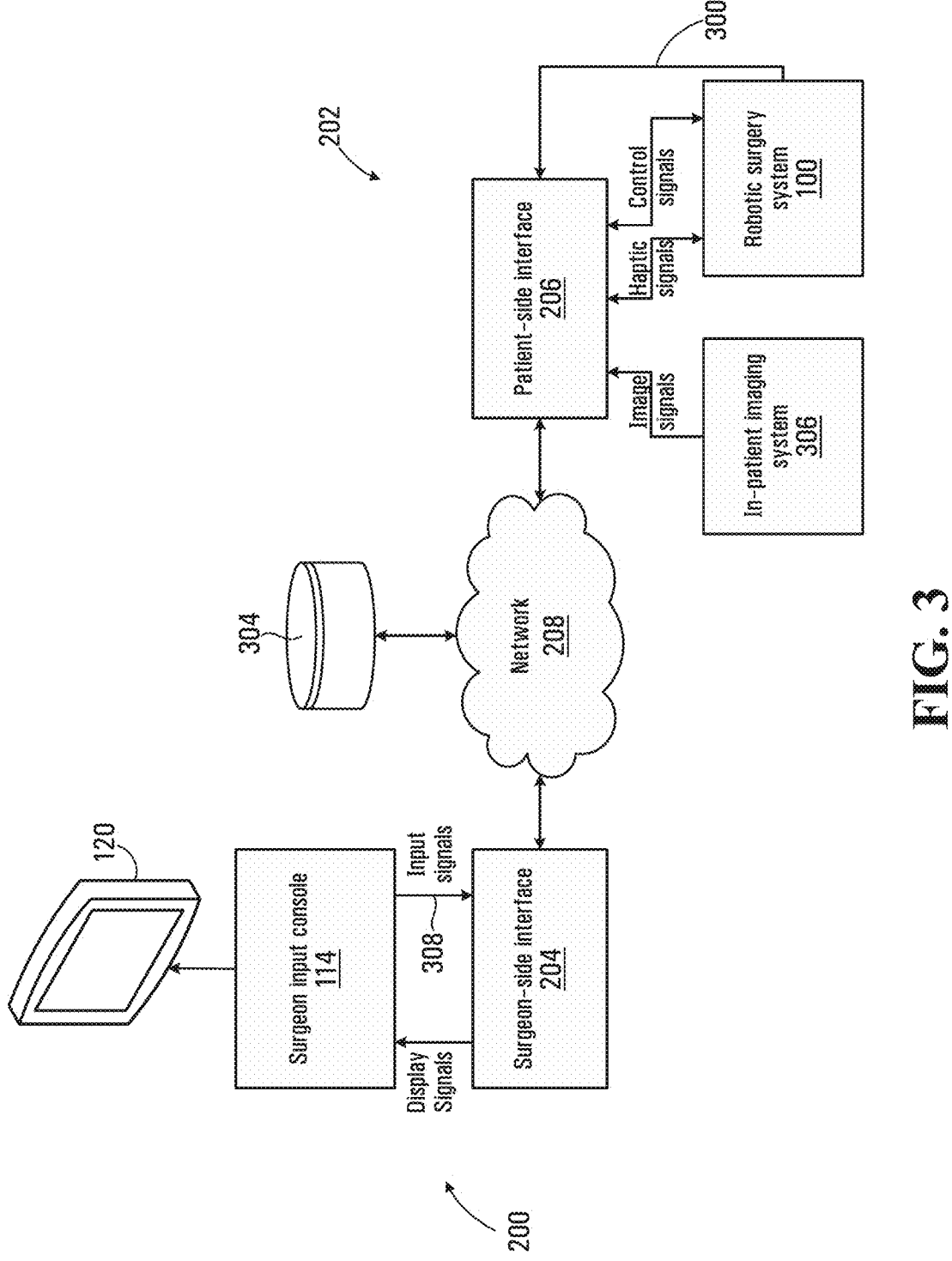
FIG. 3 is a block diagram of components of the robotic surgery system of FIG. 2.

Referring to FIG. 3, communication between the surgeon-side location 200 and patient-side location 202 are conducted via a surgeon-side interface 204 and a patient-side interface 206, which are shown schematically in FIG. 3. The surgeon-side interface 204 is connected to receive input signals from the surgeon input console 114. For example, the surgeon input console 114 may generate a stream of motion input signals 308 that represent the instantaneous position of the handles 116 within an input console workspace. Motion input signals can represent a desired movement (including position and velocity) of an instrument in the input console workspace. These motion input signals will generally be transformed via kinematic processing into signals representing desired positions and orientations of the joints of the instruments 102-108 within a surgical workspace of the robotic surgery system 100. In some instances, kinematic processing translates the position and movement of the handles 116 within the input console workspace into the position and movement of joints of the instruments 102-108. The translation can be performed by transforming the position and orientation of the handles 116 in the Cartesian coordinate system to the coordinates of the joints of the instruments 102-108 in the surgical workspace and vice versa. Other processing functions may then be used to transform these kinematically derived instrument joint positions into drive signals for actuating various actuators, such as motor servos, that cause movement of the instruments 102-108 within the surgical workspace. In the system shown in FIG. 1, the kinematic and other processing may be implemented within the surgeon input console 114 or the within robotic surgery system 100. In the implementation of FIG. 3, the input signals 308 can be picked up directly from the input devices of the surgeon input console 114 and before any kinematic or other processing has been performed. For some robotic surgery system 100, the input signals are generated by the input devices of the surgeon input console 114 at a relatively low frequency (or rate of change), for example about 200 Hz or every 5 milliseconds or about 30 Hz or less. The input signals 308 thus require a relatively low bandwidth or data rate for transmission. In contrast, post-kinematics and other processing signals may have a significantly higher frequency (or rate of change). As an example, in some robotic surgery systems the servo rate at the motor controller may be in the region of about 10 kHz or more, which may require a significantly higher bandwidth or data rate for transmission than the motion input signals generated at the input device.

In general, remotely controlling a robotic surgery system can be achieved by transmitting from the surgeon-side interface 204 to the patient-side interface 206 a complete set of signals that control the instruments 102-108 (which include at least one imaging system). Such signals may be referred to as control signals. To reduce delay and guarantee reliability of the transmission, such set of signals can include signals having the lowest frequency (or rate of change) among a plurality of available signals. As described above, input signals 308 can be transmitted from the surgeon-side interface 204 to the patient-side interface 206, rather than signals generated as a result of kinematic processing that generates signals representing desired coordinates of the joints of the instruments 102-108 in the surgical workspace associated with the robotic surgery system 100 or the drive signals (such as, torque) for actuating the motors of the instruments 102-108. In some cases, the surgeon-side interface 204 can select input signals 308 for transmission from the plurality of available signals, which can include signals generated as a result of kinematic processing and the drive signals.

In certain implementations, one or more signals generated as a result of kinematic processing may be transmitted by the surgeon-side interface 204 to the patient-side interface 206. These signals can be transmitted along with the input signals 308.

The physician-side interface 204 is in communication with the patient-side interface 206 over the network 208. The patient-side interface 206 is in communication with the robotic surgery system 100 for receiving and delivering control signals to the robotic surgery system. The patient-side location 202 also includes an in-patient imaging system 306, which generates images of the surgical site within the patient. As described above, one of the surgical instruments 102-108 may be configured to generate the in-patient images or a separate imaging system may be employed. The in-patient imaging system 306 generates data representing image frames, which is encoded into an image data stream by the patient-side interface 206 and transmitted over the network 208 to the physician-side interface 204. Image data can be encoded using hardware circuitry of the patient-side interface 204, such as one or more processors, one or more graphics processing units (GPUs), one or more field-programmable gate arrays (FPGAs), or one or more application-specific integrated circuits (ASICs). Image data can include different types of images obtained by different imaging systems. For example, image data can include endoscopic image (or video) data and X-ray images obtained by a fluoroscopy imaging system. Image data can alternatively or additionally include X-ray images obtained by a radiography imaging system, CT images obtained by a CT imaging system, ultrasound images obtained by an ultrasound imaging system, or MRI images obtained by an MRI imaging system. Different types of image data can be encoded into the image data stream for transmission over the network 208 to the physician-side interface 204. The physician-side interface 204 receives and decodes the image data stream to recover the image frame data, which is sent via the physician input console 114 to the display 120 associated with the physician input console 114. The physician 112 is able to view the surgical site on the display 120 and cause movements of the handles 116 of the physician input console 114, which are encoded by the input devices and delivered as control signals to the patient-side interface 206.

The robotic surgery system 100 may be additionally configured to generate haptic feedback and/or force feedback signals. In robotic surgery, haptic feedback signals may be generated to alert the physician 112 when an attempt is made to move one of the instruments 102-108 against an instrument movement boundary or other impediment to motion. Haptic signals may also be generated when two of the instruments 102-108 are moved toward a collision condition. These haptic signals are generally used to deliver haptic feedback via the handles 116 of surgeon input console 114 that alert the surgeon 112 to the condition. Additionally, some robotic systems may also be configured to generate force feedback signals that can be used to deliver force feedback to the surgeon via the input console 114. The force feedback may serve to indicate that the surgeon 112 is attempting to move one of the instruments 102-108 against a limitation such as human tissue or an organ. In some implementations the patient-side interface 206 may be configured to receive the haptic or force feedback signals and transmit the signals back to the surgeon-side interface 204 for delivery to the surgeon input console 114.

The network 208 may be provided as a connection to the Internet. In some cases, the network 208 may be a dedicated network such as a point-to-point fiber or a specially-conditioned and monitored network that aims to reduce transmission delay and increase reliability and stability. The network 208 can be a wide-area network (WAN). The surgeon-side interface 204 is in communication with the robotic surgery system 100 at the patient-side location 202 via the network 208.

A data store 304 can be included in communication with the network 208. The data store 304 may be used as remote network storage for storing data logs and other information connected with surgical operations performed by the systems shown.

The robotic surgery system 100 may from time-to-time generate event-oriented notifications at the patient-side location. Each event-oriented notification at the patient-side location 202 may be processed to generate a notification record including a timestamp indicating a time at which the event-oriented notification was generated, status information including information indicating a processing status of the event-oriented notification, and timeout information including information indicating an expiry time by which the event-oriented notification should be processed. These notification records are then transmitted to the surgeon-side location 200. At the surgeon-side location 200, each notification record is received and accumulated for processing.

When the status in the notification record indicates that the notification record has not yet been communicated to the surgeon input console and the expiry time in the timeout information exceeds the current time at the surgeon-side location 200 (for instance, as maintained by the surgeon-side interface 204), an alert is generated. When the status indicates that the notification record has not yet been communicated to the surgeon input console and the expiry time does not yet exceed the current time at the surgeon-side location 200, a notification message is generated and communicated to the surgeon input console. The status in the notification record is then changed to indicate that the notification record has been processed.

In some implementations, the robotic surgery system 100 may be expecting the control signals to be provided at a certain threshold rate (such as, the rate of a patient-side synchronization signal (PSS) signal 300). When the control signals received by the robotic surgery system do not satisfy such threshold rate, the patient-side interface 206 can repeat at least some of the received control signals or otherwise modify the control signals in order to provide the control signals to the robotic surgery system 100 at the threshold rate. The threshold rate may not be satisfied as a result of control signals not being received by the patient-side interface 206 at a sufficient rate (because of, for instance, network delay) or due to one or more control signals having been discarded, among others.

In certain cases, the robotic surgery system 100 can transmit acknowledgment information to the surgeon input console 114, for instance, in response to receiving control signals. Acknowledgment information can be transmitted as an acknowledgment signal or message. For example, the robotic surgery system 100 may acknowledge each control signal message or packet with an acknowledgment message. The surgeon input console 114 may be expecting the acknowledgment message to be provided at a certain threshold rate (for instance, corresponding to the rate of transmission of packets to the patient-side location 202). When the acknowledgment messages received by the surgeon input console do not satisfy such threshold rate, the surgeon-side interface 204 can repeat at least some of the received acknowledgment messages or otherwise modify the acknowledgement messages in order to provide the acknowledgment messages to the surgeon-side interface 204 at the threshold rate. The threshold rate may not be satisfied as a result of acknowledgment messages not being received by the surgeon-side interface 204 at a sufficient rate (because of, for instance, network delay) or due to one or more acknowledgment messages having been discarded, among others.

The surgeon-side interface 204 can be integrated with the surgeon input console 114, which can encompass being wholly separate from the surgeon input console 114 or being wholly or partially a portion of the surgeon input console 114. In some implementations, the surgeon-side interface 204 can be implemented as software and/or firmware being executed by one or more processors of the surgeon input console 114.

The patient-side interface 206 can be integrated with the robotic surgery system 100, which can encompass being wholly separate from the robotic surgery system 100 or being wholly or partially a portion of the robotic surgery system 100. In some implementations, the patient-side interface 206 can be implemented as software and/or firmware being executed by one or more processors of the robotic surgery system 100.

System for Remotely Controlling Robotic Procedures

Figure 4:
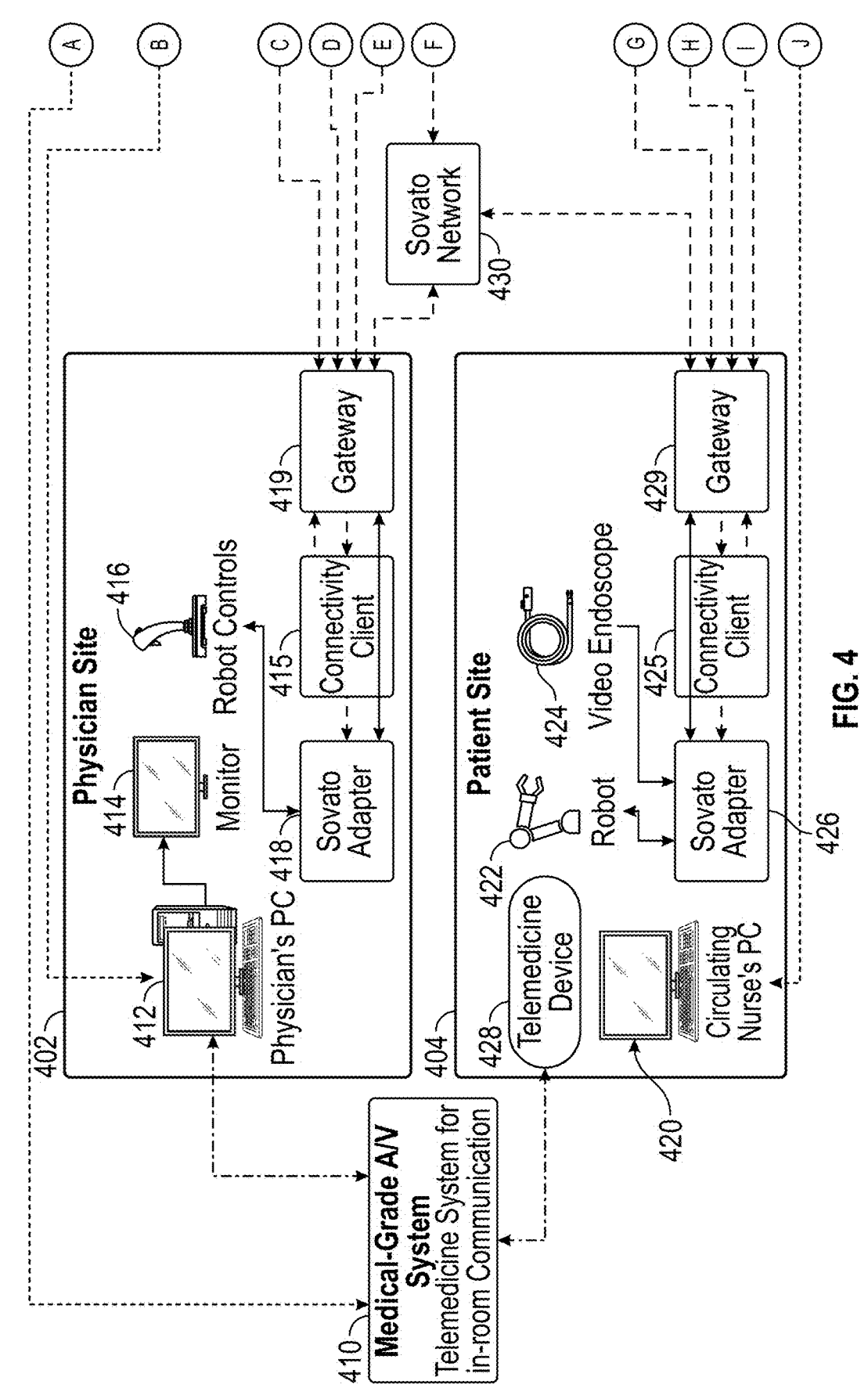
FIG. 4 is a schematic view of a remote robotic-assisted medical system.
Figure 4:
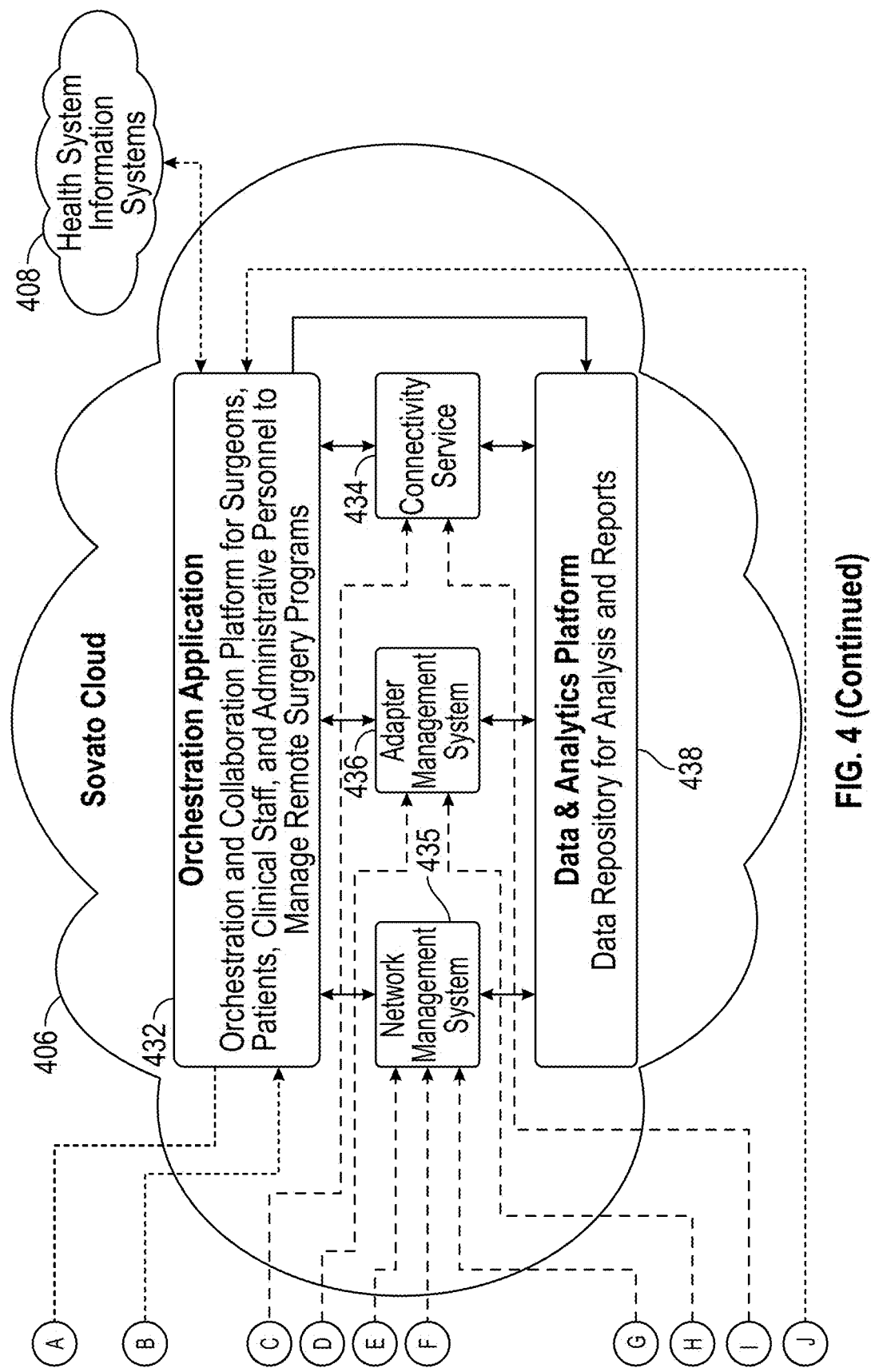

FIG. 4 illustrates a schematic view of a remote robotic-assisted medical system 400. The system 400 can include one or more physician sites 402 each having one or more computing devices 412 (such as, one or more physician personal computers (PCs)), one or more monitors 414 (which can be connected to the one or more physician PCs), one or more physician-side connectivity clients 415, one or more robot control and display systems 416 (which can be, for instance, same as or similar to the surgeon input console 114 and can be referred to as the physician input console 416), one or more physician-side adapters 418 (which can be, for instance, same as or similar to the surgeon-side interface 204), and a physician-side gateway 419. Any of the computing devices described herein can be mobile or portable.

The system 400 can further include one or more patient sites 404 (for instance, medical centers or hospitals) each having one or more computing devices 420 (such as, one or more nurse PCs), one or more medical procedure robots 422 (which can be, for instance, same as or similar to the robotic surgery system 100, and can be referred to as robot), one or more imaging systems 424 (such as, a video endoscope) that can be part of the robotic surgery system, one or more patient-side connectivity clients 425, one or more patient-side adapters 426 (which can be same as or similar to the patient-side interface 206), and a patient-side gateway 429. The system 400 can also include one or more telemedicine devices 428 configured to communicate telemedicine information and provide the physician with audio and video related to any procedures the physician is performing. The system 400 can further include a network 430 (which can utilize the network 208 as is further explained in connection with FIG. 5) connecting a physician-side adapter 418 to a patient-side adapter 426.

As described herein, the robotic surgery system can include one or more of a patient cart, vision cart, or tower. In some instances, the robotic surgery system can include a local physician input console configured to control at least one instrument or imaging device. The local physician input console can be connected to one or more of the patient cart, vision cart, or tower by a direct connection (such as, the connection 115). Any network connections to the robotic surgery system described herein can be made to the tower or local physician input console. A remote physician input console 416 can be connected to control the robotic surgery system as described herein.

To enhance safety, the robotic surgery system can include a switching circuitry that facilitates switching from local control over the direct connection to a remote control over the network. Suppose that a remote surgeon is performing a procedure using the physician input console 416 that is located remotely from the robotic surgery system and is connected to the robotic surgery system via the network. Suppose that during the procedure, one or more of the physician input console 416 or the network experiences a malfunction. A local surgeon can take over control of the procedure using a local physician input console that is connected to the robotic surgery system via the direct connection, which can be isolated from any other network (for instance, be a direct LAN). Other examples of switching control can include switching from local to remote control by a more (or less) experienced physician.

The switching circuitry can be used to efficiently and safely facilitate such a change of control from remote to local (or vice versa). The switching circuitry can operate in two modes (or states). In a first mode (which may be a default mode), the switching circuitry can allow only local control of the robotic surgery system via the local physician input console. In a second mode, the switching circuitry can allow only remote control of the robotic surgery system via the physician input console 416 connected via the network. The switching circuitry can include a multiplexer circuitry configured to switch flow of control signals, image data, and status data between the direct connection and the network.

In some implementations, the switching circuitry can be at least partially exposed on a surface of the robotic surgery system so that it can be quickly and easily manipulated by a nurse or another user. The switching circuitry can include a switch or a button. In some instances, the switching circuitry can include a graphical user interface that, for instance, displays a switch, button, checkbox, sliding control, or the like. The graphical user interface can be displayed on a touch screen display. In some instances, the switching circuitry can respond to a voice command to switch control. In some cases, the switching circuitry can be controlled remotely, such as, via a command transmitted over the network.

The switching circuitry can transition between operating in the first and second modes responsive to receiving different (or same) signals. For example, suppose that the switching circuitry is operating in the first mode (which can be a default mode), thereby allowing only local control. In response to receiving a first signal, the switching circuitry can transition to operating in the second mode, thereby allowing only remote control. In response to subsequently receiving a second signal (or again receiving the first signal again), the switching circuitry can return to operating in the first mode.

The switching circuitry can be integrated with the robotic surgery system. This can encompass being wholly separate from the robotic surgery system or being wholly or partially a portion of the robotic surgery system. In some cases, the switching circuitry can be at least partially exposed on an exterior surface of the robotic surgery system (such as, the local physician input console). In some implementations, the switching circuitry can be implemented as software and/or firmware being executed by one or more processors of the robotic surgery system. Additional details of the switching circuitry are described in U.S. patent application Ser. No. 19/273,545, filed on Jul. 18, 2025, which is incorporated by reference in its entirety.

In some cases, as described herein, a physician-side adapter 418 can be integrated with a robot control and display system 416 and/or a patient-side adapter 426 can be integrated with a robot 422. In some instances, a physician PC 412 can be integrated with a robot control and display system and/or a nurse PC 420 can be integrated with a robot 422. Being integrated with can encompass being wholly separate from a corresponding system or being wholly or partially a portion of the corresponding system. For instance, being integrated with can encompass being implemented as software and/or firmware being executed by one or more processors of the corresponding system.

The system 400 can include one or more computing devices, which can form a computing cloud 406. The cloud can implement one or more of: an orchestration server or application 432, a connectivity server 434, a network management system 435 (NMS) (sometimes referred to as (sometimes referred to as network control system or NCS), an adapter management server or system 436 (sometimes referred to as SAMS), and a data and analytics server or platform 438. The system 400 can further include a health system information systems 408, comprising a database storing electronic health records (EHR) and/or electronic medical records (EMR) relating to one or more patients. The system 400 can further include one or more medical-grade audio/visual (A/V) systems 410, which can communicate with one or more telemedicine devices 428.

As described herein, the orchestration application 432 can perform one or more of: verify credentials of a physician, provide coordination between the patient side and physician side (or verify that such coordination has been established), establish an A/V connection between the physician side and the patient side (or verify that the A/V connection has been established), verify that a time window for remotely performing a medical procedure on the patient is open, and verify that network connection satisfies one or more conditions. As described herein, the connectivity server 434 can track network addresses of the physician-side adapters 418 and the patient-side adapters 426 and establish a connection between a physician-side adapter and a patient-side adapter. As described herein, the adapter management system 436 can perform adapter monitoring and management. For example, the health of the adapters can be verified and tracked.

A physician PC 412 can be operably connected to a medical-grade A/V system 410 and the orchestration application 432. In an example, the physician PC 412 can communicate telemedicine information and provide the physician with audio and video related to any robotic procedures the physician is conducting. For example, the physician PC 412 can display to the physician on a monitor 414 a real-time video of a patient site 404, the premises where a medical procedure will take place, is being performed, or has been performed. The monitor 414 can display such footage in response to the medical-grade A/V system 410 providing video footage of the patient site 404 to the physician site 402. The physician PC 412 can also be operably connected to the orchestration application 432. The physician PC 412 can transmit physician related information to the orchestration application 432. The physician related information can include information such as the physician's credentials, identification, schedule, specialties, and any access related information related to the robotic procedures the physician will perform. In some implementations, a single physician PC 412 can be used for multiple physician input consoles 416. In some cases, each physician input console 416 can have a dedicated physician PC 412 (for instance, such dedicated physician PC 412 can be connected to the physician input console 416 or its associated physician-side adapter 418 via a wired or wireless connection).

A physician-side connectivity client 415 can allow a physician-side adapter 418 to connect to the network 430 and cloud 406. The physician-side connectivity client 415 can be implemented in software and/or firmware being executed by one or more processors of the physician-side adapter 418. The physician-side connectivity client 415 can call one or more application programming interfaces (APIs) to connect the physician-side adapter 418 to one or more of the network management system 435, the adapter management system 436, or the connectivity server 434. In some instances, the physician-side connectivity client 415 may be implemented by a computing device that is separate from the physician-side adapter 418. In implementations that integrate the physician-side adapter 418 with the physician input console 416, the physician-side connectivity client 415 can be implemented by the physician input console 416.

A physician-side connectivity client 415 (or a physician-side adapter 418) can be assigned an internal internet protocol (IP) address and an external IP address. The internal IP address can correspond to an IP address with respect to a local network of a physician site 402. The external IP address can correspond to an IP address outside of that local network (such as, IP address on the network 430). The physician-side connectivity client 415 can communicate with the cloud 406 via the network 430 and provide information (such as, the internal IP address and the external IP address) to initiate a connection with a patient-side connectivity client 425. The information to initiate a connection with the patient-side connectivity client 425 can include one or more of: an identifier of the physician-side adapter 418, an internal IP address of the physician-side connectivity client 415, or any or information needed to establish a connection with the patient-side connectivity client 425.

A physician input console 416 can include a visual display to show the physician visual indications relating to the robotic procedure. The physician input console 416 can be operably coupled to a physician-side adapter 418. The physician input console 416 can display a view of the robotic procedure site (for instance, as detected by an imaging system 424) and/or any other component relevant to the robotic procedure. A monitor 414 can display visual indicators representing a strength of signal connectivity to the components in the patient site 404. In another example, the monitor 414 can display device characteristics regarding the physician input console 416 and/or the robot 422.

As described in connection with a physician input console 114, a physician input console 416 can include one or more devices used to control one or more medical procedure robots. The physician input console 416 can be operably coupled to a physician-side adapter 418. In an example, robot controls of the physician input console 416 can control movement, actuation, clutch, or any other relevant feature for a medical procedure robot to perform robotic procedures. The physician input console 416, and the corresponding console, can include a type. The type can correspond to the manufacturer of the physician input console, model of the physician input console, and/or version of the software or firmware being executed by one or more processors or the physician input console 416. For example, the manufacturer of the physician input console 416 can include Intuitive Surgical, Medtronic, or any other manufacturer of a physician input console. As another example, the model of the physician input console 416 can include Da Vinci Xi, Da Vinci X, or Da Vinci SP manufactured by Intuitive Surgical.

A physician-side adapter 418 can include a physical device, program, application, application programming interface (API), software development kit (SDK), or another device or program to allow remote robotic procedure. In some implementations, the physician-side adapter 418 can be software and/or firmware being executed by one or more processors of a physician input console 416. The physician-side adapter 418 can be operably coupled to a patient-side adapter 426 via the network 430 and/or the cloud 406, including the connectivity server 434 and the adapter management system 436. In an example, the physician-side adapter 418 can include a device operably coupled to the physician input console 416, to interface the physician input console 416 to the cloud 406 and the network 430. In this example, the physician-side adapter 418 can include hardware components and software components to receive communication signals from the physician input console 416. In this example, the physician-side adapter 418 (or a physician-side connectivity client 415) can include an internal internet protocol (IP) address. The internal IP address can correspond to an IP address with respect to a local network of a physician site 402.

A physician-site adapter 418 and/or a patient-side adapter 426 can be configured software-defined wide-area network (SD-WAN) devices. The network 430 can be configured as SD-WAN network connecting such SD-WAN devices. Internal IP addresses can be used to communicate with devices on the SD-WAN. The internal IP address can be used to establish the connection for remote robotic procedure since the adapters would be part of the same WAN, and external IP addresses may not need to be used. Any other components of the system 400, such as an A/V system 410, physician PC 412, nurse PC 420, or telemedicine device 428, can be similarly configured as SD-WAN devices and become part of the SD-WAN.

Physician-side gateway 419 can forward network traffic between one or more physician-side connectivity clients 415 at a physician site 402 and the network 430. A physician-side connectivity client 415 can be connected to the physician-side gateway 419 via a suitable network connection available at the physician site 402, such as LAN (for instance, implemented using Ethernet or Wi-Fi). In some instances, the physician-side gateway 419 may not be present, and the physician-side connectivity client 415 can be directly connected to the network 430.

When multiple physician input consoles 416 are present at the physician site 402, each can be connected directly or through one or more of its dedicated physician-side adapter 418 or physician-side connectivity client 415 to the physician-side gateway 419 via a dedicated network connection (such as, via a dedicated Ethernet cable plugged into a port in the physician-side gateway 419). This dedicated network connection can be a LAN. In this arrangement, no physician input console shares, at a physician site, any network connection (such as, LAN) with any other physician input console and each physician input console has its own dedicated network connection to a physician-side gateway. The physician-side gateway 419 can be a single gateway with sufficient number of ports to connect all physician input consoles or a collection of gateways.

A nurse PC 420 can also be operably connected to the orchestration application 432. The nurse PC 420 can transmit patient related information to the orchestration application 432. The patient related information can include the patient's health records, identification, schedule, notes, and any access related information related to the robotic procedures the patient can receive. In some implementations, a single nurse PC 420 can be used for robots 422. In some cases, each robot 422 can have a dedicated nurse PC 420 (for instance, such dedicated nurse PC 420 can be connected to the robot 422 or its associated patient-side adapter 426 via a wired or wireless connection).

A robot 422 can include one or more robotic devices used to perform robotic procedures. The robot 422 can be operably coupled to a patient-side adapter 426. In an example, the robot 422 can receive controls to perform movement, actuation, power, and any other relevant feature to perform a robotic procedure. The robot 422, and any corresponding devices, can include a type. The type can correspond to the manufacturer of the robot, model of the robot, and/or version of the software or firmware being executed by one or more processors of the robot 422. For example, the manufacturer of the robot 422 can include Intuitive Surgical, Medtronic, or any other manufacturer of medical procedure robots. As another example, the model of the robot 422 can include Da Vinci Xi, Da Vinci X, or Da Vinci SP manufactured by Intuitive Surgical.

An imaging system 424 can communicate video to the physician related to any robotic procedures the physician is performing. The imaging system 424 can be operably coupled to the patient-side adapter 426 (directly or through the robot 422). In an example, the imaging system 424 can provide to the physician site 402 a view of a robotic procedure site. The view can include a real-time perspective of the patient before, during, or after robotic procedure is performed.

A patient-side connectivity client 425 can allow a patient-side adapter 426 to connect to the network 430 and cloud 406. The patient-side connectivity client 425 can be implemented in software and/or firmware being executed by one or more processors of the patient-side adapter 426. The patient-side connectivity client 425 can call one or more APIs to connect the patient-side adapter 426 to one or more of the network management system 435, the adapter management system 436, or the connectivity server 434. In some instances, the patient-side connectivity client 425 may be implemented by a computing device that is separate from the patient-side adapter 426. In implementations that integrate the patient-side adapter 426 with the robot 422, the patient-side connectivity client 425 can be implemented by the robot 422.

A patient-side connectivity client 425 (or a patient-side adapter 426) can include an internal IP address and an external IP address. The internal IP address can correspond to an IP address with respect to a local network of a patient site 404. The external IP address can correspond to an IP address outside of that local network (such as, IP address on the network 430). The information to initiate a connection with the physician-side connectivity client 415 can include one or more of: an identifier of the patient-side adapter 426, an internal IP address of the patient-side connectivity client 425, or any other information needed to establish a connection with the physician-side connectivity client 415.

A patient-side adapter 426 can be operably coupled to a physician-side adapter 418 via the network 430 and/or the cloud 406. The patient-side adapter 426 can include one or more of a physical hardware, program, application, API, SDK, or another device or program to allow remote robotic procedures. For example, patient-side adapter 426 can include a device operably coupled to a robot 422 to interface the robot 422 to the cloud 406 and the network 430. In this example, the patient-side adapter 426 can include hardware components and software components to receive communication signals from the robot 422 and establish a network connection to the network 430 and the cloud 406. In some implementations, the patient-side adapter 426 can be software and/or firmware being executed by one or more processors of the robot 422. Similarly to a physician-side adapter 418, the patient-side adapter 426 can include an internal IP address and an external IP address. As described herein, one or more of such IP addresses can be utilized to establish a connection with the physician-side adapter. The information to initiate a connection with the physician-side adapter 418 can include an identifier of the patient-side adapter 426, an internal IP address of the patient-side adapter 426, an external IP address of the physician-side adapter 418, and/or any or information relevant to establish a connection with the patient-side adapter 426. As described herein, the patient-side adapter 426 can be configured as SD-WAN device and its internal IP address can be used to establish the connection.

A telemedicine device 428 can communicate telemedicine information and provide a physician with audio and video related to any robotic procedures the physician is performing. The telemedicine device 428 can be operably coupled to a medical-grade A/V system 410. In an example, the telemedicine device 428 can provide to the physician site 402 a view of the patient site 404 (such as, an operating room). The view can include a real-time perspective of the patient before, during, or after a procedure is performed. In another example, the telemedicine device 428 can receive information from a physician PC 412 through the medical-grade A/V system 410. For example, the telemedicine device 428 can receive information related to the procedure, including one or more of a notice regarding the physician's readiness, status of connectivity, updated patient health records, or scheduling information. In this example, the related information can include the physician's credentials, identification, schedule, specialties, and any access related information related to the robotic procedures the physician will perform. In another example, the telemedicine device 428 can further include an A/V system including a third-party telemedicine hardware provider and medical cart. The A/V system 410 and/or the telemedicine device 428 can facilitate provision of an audio and/or video feed from the patient site 404 to a physician site 402 (and vice versa) as well as facilitate a two-way audio and/or video communication between the patient site 404 and the physician site 402. In some instances, a two-way audio communication between the patient site 404 and the physician site 402 and a one-way video communication from the patient site 404 to the physician site 402 can be utilized.

Patient-side gateway 429 can forward network between one or more patient-side connectivity clients 425 at a patient-site 404 and the network 430. A patient-side connectivity client 425 can be connected to the patient-side gateway 429 via a suitable network connection available at the patient site 404, such as LAN. In some instances, the patient-side gateway 429 may not be present, and the patient-side connectivity client 425 can be directly connected to the network 430.

When multiple robots 422 are present at the patient site 404, each can be connected directly or through one or more of its dedicated patient-side adapter 426 or patient-side connectivity client 425 to the patient-side gateway 429 via a dedicated network connection (such as, via a dedicated Ethernet cable plugged into a port in the patient-side gateway 429). This dedicated network connection can be a LAN. In this arrangement, no robot shares, at a patient site, any network connection (such as, LAN) with any other robot and each robot has its own dedicated network connection to a patient-side gateway. The patient-side gateway 429 can be a single gateway with sufficient number of ports to connect all robots or a collection of gateways.

The network 430 can connect the physician-side adapter 418 and the patient-side adapter 426. The network 430 can be configured as SD-WAN to provide connectivity between the physician-side adapter 418 and the patient-side adapter 426. The network 430 can facilitate a peer-to-peer connection between a physician-side adapter 418 and a patient-side adapter 426. Such peer-to-peer connection can allow the physician-side adapter 418 and the patient-side adapter 426 to transmit and receive information and instructions (such as, in the form of data packets) directly. The information can include robot control instructions and feedback sensor information, real-time patient information including medical health monitoring statuses, patient-side video endoscope content (for example, from the imaging system 424), network connectivity strength including a primary and alternate network connectivity options (for example, SD-WAN, 5G, Ethernet, fiber optic, satellite communication, or any other type of connection available), and any other information relevant to the peer-to-peer network connection.

There can be several ways for establishing a connection via the network 430. For example, a physician-side adapter 418 can request connection to a patient-side adapter 426 from the connectivity server 434. For example, the physician-side adapter 418 can transmit a request to the connectivity server 434 and receive the patient-side adapter 426 internal IP address from the connectivity server 434. In this example, the physician-side adapter 418 can then request to establish a connection (such as, a direct peer-to-peer connection) with the patient-side adapter 426.

As another example, a physician-side adapter 418 can request a connection to a patient-side adapter 426 from the adapter management system 436. For example, the physician-side adapter 418 can transmit a request to the connectivity server 434 and receive the patient-side adapter 426 internal IP address from the adapter management system 436. In this example, the physician-side adapter 418 can then request to establish a connection (such as, a direct peer-to-peer connection) with the patient-side adapter 426. While these examples describe that the physician-side adapter 418 initiates the connection to the patient-side adapter 426, the patient-side adapter 426 can similarly initiate the connection in some implementations.

In any of these examples, external IP address(es) can also be used to establish the connection. As described herein, external IP address(es) can be used when the adapters are not part of the same network (such as, not part of the same SD-WAN).

The connection can be established in response to: 1) verification of login credentials of a physician, 2) completion of coordination between the physician side and patient side (such as, completion of one or more handshake protocols), 3) establishment of a two-way audio communication between the physician side and the patient side, 4) establishment of a video communication from at least the patient side to the physician side, 5) verification of compatibility of physician input console and robot, and 6) verification that the network connection satisfies one or more network conditions (such as, one or more of a network latency threshold, network jitter threshold, network packet loss threshold, and network bandwidth threshold). In some instances, the connection can be established in response to ensuring that at least one of the foregoing conditions, at least two of the forgoing conditions, at least three of the foregoing conditions, at least four of the foregoing conditions, or all of the foregoing conditions have been satisfied. In some cases, the orchestration application 432 can perform the verifications.

A connection establishment protocol can be implemented to form the connection. The connection establishment protocol can be coordinated by the orchestration application 432, for instance, responsive to a request to start a session received from a patient side or physician side. The request can be received through a user interface provided by a physician PC 412 or nurse PC 420. Responsive to the request, conditions for establishing the connection can be verified (as described herein). After it has been verified that the connection can be established, the orchestration application 432 can transmit a request to initiate the connection. The request to initiate the connection can include identifiers of a physician-side adapter 418 and patient-side adapter 426 (for instance, IP addresses of the physician-side adapter 418 and patient-side adapter 426, as described herein). The request to initiate the connection can be transmitted to the connectivity server 434, which can forward a request to begin connection to the physician-side adapter 418. The connectivity server 434 can forward the request to begin connection to the IP address of the physician-side adapter

418. In response to receiving the request to begin connection, the physician-side adapter 418 can generate an offer to connect. The offer can be transmitted to the connectivity server 434, which can forward the offer to the patient-side adapter 426 (for instance, to the IP address of the patient-side adapter 426). The connection can be established responsive to the patient-side adapter 426 receiving the offer.

In some implementations, the network 430 can facilitate server-based connectivity (rather than peer-to-peer connectivity). For example, both adapters 418 and 426 can transmit data packets through the connectivity server 434 to communicate with each other.

In some examples, the system 400 can assess whether a type of a robot 422 is compatible with a physician input console 416. In this example, the system 400 will compare the types of the robot 422 and the physician input console 416 to ensure the types are compatible (such as, the same) prior to providing information to establish a connection between the robot 422 and the physician input console 416. In this example, when the robot 422 is of a first type and the physician input console 416 are of the first type, the system 400 will provide over the network 430 information to one or both of the robot 422 and the physician input console 416 to allow the devices to establish a connection (such as, a peer-to-peer connection) for remotely controlling the robot 422. Such connection can be established between the physician-side adapter 418 and the patient-side adapter 426. In another example, when the robot 422 is of a first type and the physician input console 416 are of a second type that is different from the first type, the system 400 will restrict provision of the information over the network 430 and prevent the devices from establishing the connection.

It should be noted that a preliminary maintenance connection may be formed via the network 430 between a physician-side adapter 418 and a patient-side adapter 426 prior to forming the operational connection for remotely controlling the robot 422. The preliminary maintenance connection can be used by the physician-side adapter 418 and the patient-side adapter 426 for exchanging information related to discovery, status, keeping the preliminary connection alive, or the like. This type of connection can be distinct from an operational connection (where the operational connection may be otherwise known as a "session") for remotely controlling the robot 422 during which the following types of data would be transmitted: control signals (or control commands) transmitted from the physician side to the patient side for moving and/or controlling one or more instruments or imaging systems of a robot 422, status information transmitted from the patient side to the physician side or from the physician side to the patient side (such as, heartbeat signal or other data for ensuring safety), and image data of the procedure site transmitted from the patient side to the physician side. When the operational connection for remotely controlling the robot 422 is established between a physician-side adapter 418 and a patient-side adapter 426, all these three types of data would be exchanged between the physician side and patient side.

Status information can include transmission of signals from the patient side to the physician side and from the physician side to the patient side for monitoring the status of the system 400. For example, the patient side can transmit to the physician side status information indicating that it is operating normally (for instance, this can be a heartbeat signal). As another example, the physician side can transmit to the patient side status information that it is operating normally.

In some instances, a connection for remotely controlling a robot 422 would not be established (and the three types of data described herein would not be exchanged) unless there has been coordination between the patient side and physician side. Coordination can include one or more of performing safety checks (such as, compatibility between the types of the physician input console 416 and the robot 422), ensuring that the patient site (such as, the operating room) and robot 422 have been prepared for a medical procedure, ensuring that the patient has been prepared for the procedure, or the like. In some cases, coordination can be performed by the system 400 and may include completion of or more checklists on the patient side (for instance, by a circulating nurse) and attestation by the physician that the one or more checklists have been completed correctly (such as, by clicking "Attest" on a user interface displayed on the monitor 414). A checklist can be completed on a nurse PC 420, transmitted to the physician side via the network 430, displayed on a physician PC 412, and attested to by the physician through the physician PC 412.

In some instances, at least some types of data related to the connection may be transmitted prior to establishing a connection for remotely controlling a robot 422. For example, image data of the procedure site may be transmitted to help the physician prepare for a procedure (such as, plan the procedure). Transmission of control signals and status information may be commenced at the same time.

A session for remotely controlling the robot 422 can be associated with a time window during which a physician is allowed to remotely control the robot 422 to perform a medical procedure on a patient, subsequent to a completion of coordination (such as, signoffs) as described herein. The time window can correspond to the scheduled time of the medical procedure (such as, to an allotted session time slot). After such time window has opened and over duration of the time window, the operational connection from the physician input console 416 to remotely control the robot 422 may be allowed, subsequent to the completion of coordination, while an operational connection from any other physician input console to remotely control the robot 422 may be disallowed. After the time window has ended, an operational connection from the physician input console 416 to remotely control the robot 422 may be disallowed as it is possible that another time window has been opened to permit the same or another physician input console to connect to the robot 422 to remotely control the robot to perform a medical procedure on a different patient. That is, time windows for remotely controlling a particular robot can be arranged in non-overlapping chronological order. The operational connection may be initiated responsive to completion of the coordination between the patient side and physician side, which, as described herein, can involve completion of one or more checklists and attestation of the one or more checklists (this can be referred to as signoffs). The physician can be informed that the time window has been opened, for instance, via the surgeon PC 412 and the monitor 414 (such as, via a status being shown on a schedule). In response to the notification, the physician can initiate the operational connection to remotely control the robot (for instance, by clicking "Attest" on the user interface displayed on the monitor 414). On the patient side, the clinical staff can be informed that the time windows have been opened, for instance, via the nurse PC 420.

The orchestration application 432 can include an orchestration and collaboration platform for physicians, patients, clinical staff, and administrative personnel to manage remote robotic procedure programs. The orchestration application 432 can be executed on one or more remote servers in the cloud 406 and can be operably connected to the health system information system 408, one or more A/V systems 410, one or more physician PCs 412, one or more nurse PCs 420, connectivity server 434, the adapter management system 436, the data and analytics platform 438, and the network management system 435. In some examples, the orchestration application 432 is configured to assess whether a type of a robot 422 is compatible with a physician input console 416.

The assessment of compatibility can occur prior to or at a time of a procedure. For example, the system 400 (such as, via the orchestration application 432) can assess the compatibility at the time the procedure is scheduled, which can be well before the time of procedure (such as, hours, days, or weeks) and well before the connection for remotely controlling the robot 422 is established between the adapters 418 and 426. As a safety check, compatibility may be verified again prior to forming the connection.

In another example, the system 400 can assess compatibility at the time of procedure (such as, close to the initiation of the connection). This can be performed minutes or even seconds prior to the procedure.

The process for the orchestration application 432 to assess the compatibility between a robot 422 and the physician input console 416 can be an automated process, where there is no user intervention to begin the assessment of the compatibility. For example, the orchestration application 432 can pre-verify compatibility of the types prior to when the connection for remotely controlling the robot 422 is established.

The system 400 (such as, via the orchestration application 432) can compare the types of a robot 422 and a physician input console 416 to ensure the types are compatible prior to establishment of the connection for remotely controlling the robot 422. For example, when the robot 422 is of a first type and the physician input console 416 are of the first type, the orchestration application 432 can provide over the network 430 information to one or both of the patient-side adapter 426 and physician-side adapter 418 to allow the devices to establish a connection (such as, a peer-to-peer connection). In another example, when the robot 422 is of a first type and the physician input console 416 are of a second type that is different from the first type, the orchestration application 432 will restrict provision of the information over the network 430 and prevent the devices from establishing the connection.

The connectivity server 434 can include a network signaling server. The connectivity server 434 can be operably coupled to one or more physician-side adapters 418, one or more patient-side adapters 426, the orchestration application 432, and the data and analytics platform 438. The connectivity server 434 can provide a service of connecting the physician-side adapter 418 and the patient-side adapter 426.

For example, the connectivity server 434 can receive a request from a physician-side adapter 418 to establish a connection with a patient-side adapter 426 (or vice versa). In this example, the connectivity server 434 can obtain the physician-side adapter 418 information, including an identifier, an external IP address (if needed), an internal IP address and patient-side adapter 426 information, including an identifier, an external IP address (if needed), and an internal IP address. The connectivity server 434 can obtain the physician-side adapter 418 information from the physician-side adapter 418 and/or from the adapter management system 436. In this example, the connectivity server 434 can also receive an identifier of the patient-side adapter 426 from the physician-side adapter 418, indicating the patient-side adapter 426 with which to establish a connection. The connectivity server 434 can then transmit a request to the patient-side adapter 426, to determine whether the patient-side adapter 426 is capable of establishing a connection to the physician-side adapter 418 over the network 430. In response to receiving an approval from the patient-side adapter 426, the connectivity server 434 can transmit the patient-side adapter 426 information to the physician-side adapter 418 to allow the physician-side adapter 418 to establish a connection between the adapters (for example, via the network 430). In this example, the connectivity server 434 can transmit the patient-side adapter 426 identifier, internal IP address, and external IP address (if needed). The connectivity server 434 can provide a threshold security procedure to assess whether the physician-side adapter 418 has authorization to establish a connection with the patient-side adapter 426. In this example, the connectivity server 434 can include an access control list of authorized adapters and compare the identifier of the physician-side adapter 418 to verify authorization.

In another example, the connectivity server 434 can receive a request from a patient-side adapter 426 to establish a connection with a physician-side adapter 418. The connectivity server 434 can also obtain the patient-side adapter 426 information, including an identifier, an external IP address (if needed), an internal IP address and patient-side adapter 426 information, including an identifier, an external IP address (if needed), and an internal IP address. The connectivity server 434 can obtain the patient-side adapter 426 information from the patient-side adapter 426 and/or from the adapter management system 436. The connectivity server 434 can also receive an identifier of the physician-side adapter 418 from the patient-side adapter 426, indicating the physician-side adapter 418 with which to establish a connection. The connectivity server 434 can then transmit a request to the physician-side adapter 418, to determine whether the physician-side adapter 418 is capable of establishing a connection to the patient-side adapter 426 over the network 430. In response to receiving an approval from the physician-side adapter 418, the connectivity server 434 can then transmit the physician-side adapter 418 information to the patient-side adapter 426 to allow the patient-side adapter 426 to establish a connection between the adapters (for example, via the network 430). In this example, the connectivity server 434 can transmit the physician-side adapter 418 identifier, internal IP address, and external IP address (if needed). The connectivity server 434 can provide a threshold security procedure to assess whether the patient-side adapter 426 has authorization to establish a connection with the physician-side adapter 418. In this example, the connectivity server 434 can include an access control list of authorized adapters and compare the identifier of the patient-side adapter 426 to verify the authorization.

In another example, the connectivity server 434 can receive a request from the orchestration application 432 to establish a connection between a physician-side adapter 418 and a patient-side adapter 426. The connectivity server 434 can obtain the physician-side adapter 418 information, including an identifier, an external IP address (if needed), an internal IP address and patient-side adapter 426 information, including an identifier, an external IP address (if needed), and an internal IP address. The connectivity server 434 can obtain the information from the adapters and/or from the adapter management system 436. For instance, the connectivity server 434 can receive the patient-side adapter 426 identifier from the orchestration application 432 to establish a connection between the patient-side adapter 426 and the physician-side adapter 418. The connectivity server 434 can then transmit a request to the physician-side adapter 418 to determine whether the physician-side adapter 418 is capable of establishing a connection to the patient-side adapter 426 over the network 430. In response to receiving approval from the physician-side adapter 418, the connectivity server 434 can then transmit the physician-side adapter 418 information to the patient-side adapter 426 to allow the physician-side adapter 418 to establish a connection between the adapters (for example, via the network 430). In this example, the connectivity server 434 can transmit the physician-side adapter 418 identifier, internal IP address, and external IP address (if needed) for the patient-side adapter 426 to establish a connection with the physician-side adapter 418. The connectivity server 434 can provide a threshold security procedure to assess whether the adapters have authorization to establish a connection across the network 430. The connectivity server 434 can include an access control list of authorized adapters and compare the identifiers of the adapters to verify authorization.

The adapter management system 436 can provide adapter monitoring and management. The adapter management system 436 can be operably coupled to one or more physician-side adapters 418, one or more patient-side adapters 426, the orchestration application 432, and the data and analytics platform 438. In an example, the adapter management system 436 can store information regarding adapters connected to the cloud 406. The information stored can include identifiers, internal IP addresses, and external IP addresses (if needed) of the adapters. In this example, the adapters connected to the cloud 406 are in a trusted state (for instance, part of the same SD-WAN), such that the adapter management system 436 communicates directly with the adapters. In this example, the adapter management system 436 can communicate with the adapters as if the adapters are on the same local network, such that there is no need to communicate using an external IP address, as described herein.

The data and analytics platform 438 can include a data repository for analysis and reports, which can improve the performance of the medical procedure teams and technology that facilitates remote robotic-assisted procedures. The data and analytics platform 438 can be operably coupled to the orchestration application 432, the connectivity server 434, the network management system 435 and the adapter management system 436. The data and analytics platform 438 can store data from remote robotic procedures performed using the system 400.

The aforementioned components of the system 400 (such as, one or more of the health system information systems 408, a medical-grade A/V system 410, a physician PC 412, a monitor 414, a physician input console 416, a physician-side adapter 418, a nurse PC 420, a robot 422, an imaging system 424, a patient-side adapter 426, the cloud 406, the orchestration application 432, the connectivity server 434, the network management system 435, the adapter management system 436, connectivity clients 415 or 425, gateways 419 or 429, or the data and analytics platform 438) can be communicably coupled to each other via the network 430 and/or the cloud 406, such that data can be transmitted between the components. The network 430 and the cloud 406 can include the Internet, intranet, or other suitable network. The data transmission can be encrypted, unencrypted, over a virtual private network (VPN) tunnel, or other suitable communication means. The network 430 and the cloud 406 can be a wide area network (WAN) (such as, SD-WAN), local area network (LAN), personal area network (PAN), or another suitable network type. The network communication between any of the system 400 components can be encrypted using pretty good privacy (PGP), Blowfish, Twofish, triple data encryption standard (3DES), hypertext transfer protocol secure (HTTPS), or other suitable encryption. The system 400 can be configured to provide communication via the various systems, components, and modules disclosed herein via an application programming interface (API), peripheral component interface (PCI), PCI-Express, American National Standards Institute (ANSI)-X12, Ethernet, Wi-Fi, Bluetooth, or other suitable communication protocol or medium. Additionally, third party systems and databases can be operably coupled to the system components via the network 430 and/or the cloud 406. For example, an EHR/EMR system (such as, the system 408) can be operably coupled to the cloud 406 to transmit patient information, scheduling information relating to a procedure, physician information, or any other relevant information to perform remote robotic procedure.

The data transmitted to and from the components of system 400, can include any format, including JavaScript Object Notation (JSON), transfer control protocol (TCP)/IP, extensible markup language (XML), hypertext markup language (HTML), American Standard Code for Information Interchange (ASCII), short message service (SMS), comma-separated value (CSV), representational state transfer (REST), or other suitable format. The data transmission can include a message, flag, header, header properties, metadata, and/or a body, or be encapsulated and packetized by any suitable format having same.

The network 430 and/or the cloud 406, including the orchestration application 432, connectivity server 434, network management system 435, adapter management system 436, and data and analytics platform 438, can be implemented in hardware, software, or a suitable combination of hardware and software therefor, and may comprise one or more software systems operating on one or more servers having one or more processors with access to memory. The network 430 and/or the cloud 406, including the orchestration application 432, connectivity server 434, network management system 435 adapter management system 436, and data and analytics platform 438, can include electronic storage, one or more processors, and/or other components. The network 430 and/or the cloud 406, including the orchestration application 432, connectivity server 434, network management system 435 adapter management system 436, and data and analytics platform 438, can include communication lines, connections, and/or ports to enable the exchange of information via a network 430 and/or the cloud 406, and/or other computing platforms. The network 430 and/or the cloud 406, including the orchestration application 432, connectivity server 434, network management system 435 adapter management system 436, and data and analytics platform 438, can also include a plurality of hardware, software, and/or firmware components operating together to provide the functionality attributed herein. For example, the network 430 can be implemented by a cloud of computing platforms operating together as the network 430, including Software-as-a-Service (SaaS) and Platform-as-a-Service (PaaS) functionality. Additionally, the cloud 406 can be implemented using commercial cloud computing platforms, including all such functionality provided by the commercial cloud computing platform.

Any of the components of the system 400 can comprise electronic storage that stores information. The electronic storage can include one or both of system storage that can be provided integrally (such as, substantially non-removable)

with the network 430 and/or the cloud 406, and/or removable storage that can be removably connectable to the network 430 and/or the cloud 406 via, for example, a port (such as, a Universal Serial Bus (USB) port, a firewire port, etc.) or a drive (such as, a disk drive, etc.). Electronic storage may include one or more of optically readable storage media (such as, optical disks, etc.), magnetically readable storage media (such as, magnetic tape, magnetic hard drive, floppy drive, etc.), electrical charge-based storage media (such as, erasable electronic programmable read only memory (EE-PROM), random access memory (RAM), etc.), solid-state storage media (such as, flash drive, etc.), and/or other electronically readable storage media. Electronic storage may include one or more virtual storage resources (such as, cloud storage, a virtual private network, and/or other virtual storage resources). The electronic storage can include a database, or public or private distributed ledger (such as, blockchain). Electronic storage can store machine-readable instructions, software algorithms, control logic, data generated by processor(s), data received from server(s), data received from computing platform(s), and/or other data that can enable server(s) to function as described herein. The electronic storage can also include third-party databases accessible via the network 430 and/or the cloud 406.

Any of the components of the system 400 can include control circuitry, such as processor(s) or controller(s), configured to provide data processing capabilities, for instance, in the network 430 and/or the cloud 406. As such, any of the processors can include one or more of a digital processor, an analog processor, a digital circuit designed to process information, an analog circuit designed to process information, a state machine, and/or other mechanisms for electronically processing information, such as field programmable gate arrays (FPGAs) or application specific integrated circuits (ASICs). The processor(s) can be a single entity or include a plurality of processing units. These processing units can be physically located within the same device, or processor(s) can represent processing functionality of a plurality of devices or software functionality operating alone, or in concert. A networked computer processor can be a processor operably coupled to the network 430 and/or the cloud 406. The networked computer processor can be operably coupled to other processors, databases, or components.

The orchestration application 432, connectivity server 434, network management system 435 adapter management system 436, and data and analytics platform 438 can be configured with machine-readable instructions having one or more functional modules. The machine-readable instructions can be implemented on one or more servers, having one or more processors, with access to memory. The machine-readable instructions can be a single networked node, or a machine cluster, which can include a distributed architecture of a plurality of networked nodes. The machine-readable instructions can include control logic for implementing various functionality, as described in more detail below. The machine-readable instructions can include certain functionality associated with the system 400. Additionally, the machine-readable instructions can include a smart contract or multi-signature contract that can process, read, and write data to the database, distributed ledger, or blockchain.

Network for Remotely Controlling Robotic Procedures

Interconnecting physician input consoles and robotic systems can involve considerable expense and effort. For instance, suppose that a patient site (such as, a hospital or another suitable site) that houses one or more robots desires to allow such one or more robots to be controlled by one or more remotely located physician input consoles. To reduce transmission delay and guarantee reliability and stability of transmission, a high-quality network connection is required rather than using the public Internet, and therefore the hospital would need to design and deploy a suitable network (such as, the network 430) that provides one or more connections between the one or more robots and consoles. A physician site (such as, a medical center, physician center, or another suitable site) housing one or more physician input consoles may need to undergo a similar process. Undesirably, such undertaking can be difficult, time consuming, and expensive. Further, each hospital and physician center that wishes to provide remotely controlled robotic procedures may need to design and deploy its own network, which can lead to wasteful duplication of effort and resources.

To address these shortcomings, a network for remotely controlling robotic procedures can be designed and deployed. Such network can include one or more nodes for connecting patient sites and physician sites. A node can be referred to as a point-of-presence (POP) node (which can also be referred to as a data center). To connect to the network, patient sites and physician sites may only need to employ a suitable last mile or last kilometer connection (sometimes referred to as an onramp connection or onramp) that satisfies network requirements for remote robotic procedures (which are described herein). Last mile connection can connect a patient-side gateway or physician-side gateway to a PoP. For example, a patient site or physician site may utilize a dedicated connection (such as, a leased line) for connecting with a PoP. In some cases, an onramp connection can be a direct connection. A direct connection may not pass through any routers or switches to connect a gateway to a PoP. A direct connection can provide high performance (such as, high bandwidth, low latency, low packet loss, and low jitter). In some cases, an onramp connection can be a fiberoptic connection. The network can be a single network covering a particular geographical area or region (for instance, the continental United States or other regions). Advantageously, this approach can simplify and streamline deployment of remotely-controlled robotic systems.

Figure 6:
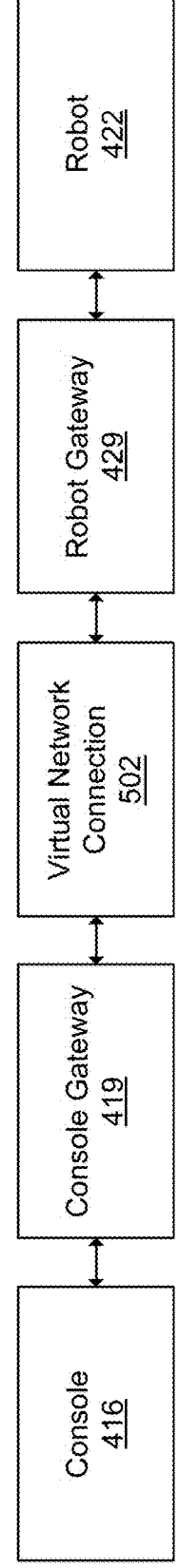
FIG. 6 illustrates a block diagram of network virtualization for remotely controlled medical procedures.

FIG. 6 illustrates a network 1000 for remotely controlling robotic procedures. The network 1000 is illustrated as covering the continental United States. Another network 1005 is illustrated as covering the continental United States, Canada, Europe, Asia, and Africa. The network 1000 can be a subset of the network 1005. The network 1000 can be a global wide area network (WAN). The network 1000 can include a plurality of POP nodes 1012, 1014, 1016, 1018, 1020, and 1022, and the network 1005 can include at least a POP node 1019. The POP nodes can serve as regional hubs for connecting patient sites and physician sites. For instance, a plurality of sites 1040 and 1042 each of which houses one or more robotic systems (which can be similar to the robot 422) and a plurality of sites 1044 and 1046 each of which houses one or more physician input consoles (which can be similar to the physician input consoles 416) can utilize the POP node 1016 for connecting to the network 1000. At the same time, a plurality of sites 1030 and 1032 each of which houses one or more physician input consoles and a patient site 1034 that houses one or more robotic systems can utilize the POP node 1018 for connecting to the network 1000. As is described herein, the sites 1030, 1032, and 1034 can each be connected to the POP node 1018 via a suitable last mile connection, and the sites 1040, 1042, 1044, and 1046 can each be connected to the POP node 1016 via a suitable last mile connection. For example, a last mile connection 1050 connects the site 1040 to the POP node 1016.

The network 1000 can guarantee that a physician input console located anywhere in an area, country, or region covered by the network can connect (provided that all other conditions described herein are satisfied) to a robotic system located in another part of the area, country, or region covered by the network. To achieve this, a POP node of the network 1000 can be connected to at least one other POP node. Some POP nodes can be connected to multiple other POP nodes, which can provide fallback allocation, failover, and redundancy. PoP nodes can be connected to one another by a backbone connection (or backbone network), such as, 1024, 1026, 1028, or 1056. A backbone connection can be a high-speed direct connection or a high-speed dedicated connection. A dedicated connection can be an exclusive connection that ensures consistent bandwidth and service quality (or, more generally, consistent performance). As described herein, a direct connection may not pass through any routers or switches and can provide high performance (such as, high bandwidth, low latency, low packet loss, and low jitter).

A POP node may be implemented as one or more servers, such as (such as, one or more servers housed in a data center) or can be implemented as software and/or firmware being executed by one or more processors, such as one or more processors of server(s). A data center can house one or more firewalls and one or more network switches (such as, fiberoptic network switches).

Suppose that a physician operating a physician console located at a site 1036 wishes to perform a remote robotic procedure on a patient using a robot located at the site 1040. A connection between the physician console and robot can span or traverse a last mile connection 1052 connecting the site 1036 to the POP node 1022, the backbone connection 1024 between POP nodes 1022 and 1016, and the last mile connection 1050 connecting the POP node 1016 to the site 1040.

As described herein, the network 1000 can be an SD-WAN.

Network Virtualization

Interconnecting physician input consoles and robotic systems can involve considerable expense and effort. For instance, suppose that a patient site (such as, a hospital or another suitable site) that houses one or more robots desires to allow such one or more robots to be controlled by one or more remotely located physician input consoles. To reduce transmission delay and guarantee reliability, security, and stability of transmission, network virtualization approaches can be used for connecting a physician input console to a robot over a physical network, such as the network 1000, that includes a plurality of different or disparate network connections (such as, multiple LANs and other networks). This can facilitate consistency, simplify management, improve scalability and flexibility, enhance security, improve resource utilization, and reduce costs.

For example, suppose a robotic system is designed for operating over a direct connection, as is illustrated in FIG. 1. For security, such robotic system operates over a direct LAN spanning a console and robot. One or more of the robot or console may be assigned a static or dynamic private IP address (such as selected from the range of 192.168.x.x to 192.168.255.255, 172.16.x.x to 172.31.255.255, or 10.x.x.x to 10.255.255.255). When such robotic system is reconfigured for remote control, communication solely over the direct LAN would be no longer possible. Instead, data communicated between the console and robot would span multiple different or disparate physical networks that use public IP addresses different from the private IP address(es) on the direct LAN. When private IP address(es) are static, the difficulties associated with communicating over multiple different or disparate physical networks may be exacerbated by having overlapping IP addresses being assigned to different consoles or robots. While IP addresses are used in certain examples, the described techniques apply to use of other types of network communication addresses or identifiers, such as media access control (MAC) addresses.

One solution to these problems would be to reconfigure the network addressing scheme used by the robotic system to accommodate different IP addresses, but this may be time consuming and error-prone particularly in cases where static IP address(es) are hard-coded into the firmware or software program that manages communication between the console and robot. Another solution to these problems would be to integrate a firewall, router, or another suitable device that implements network address translation (NAT) for communicating between the console and robot. However, these approaches would be complex to implement and scale as well as difficult to manage across multiple patient and physician sites.

To address these shortcomings and advantageously, a dynamically controlled, secure virtual network can be designed and deployed. In some implementations, the virtual network makes the console appear as though it is communicating with the robot over a direct LAN even though the console is positioned in a different geographic location and is connected to the robot by one or more different or disparate physical networks. This enables the robots and consoles to use their existing hard-coded or dynamic IP address, eliminates the need for NAT with a firewall, router, or another suitable device, and can be implemented irrespective of the distance over a network. The virtual network dynamically establishes and tears down connections as needed, thus allowing secure point-to-point or multipoint communication between consoles and robots regardless of distance. The virtual network provides security, flexibility, and ease of deployment and management.

Such virtual network can provide the ability for one or more remote physician sites to connect with a suitable network (such as, the network 430 or 1000) directly or via a gateway (such as, physician-side gateway 419) in order to establish and manage a connection with the patient site. Advantageously, this approach can make a remote physician site appear as though it is communicating with a patient site over a local LAN network, even though the connection spans multiple different or disparate networks. Further, this approach allows the preexisting static or dynamic IP addresses assigned to the one or more robots or consoles to continue to be utilized, which would allow the one or more robots or consoles to be used for remote medical procedures without needing to redesign the firmware or software of the one or more robots or consoles.

A virtual network can support multiple sessions for performing multiple medical procedures. At least some of the sessions can overlap in time or none of the sessions may overlap in time. In some cases, a different virtual network connection can be provided for each session.

FIG. 6 illustrates a block diagram of a session 500 between a physician console (such as a console 416) and a robot system (such as a robot 422) for remotely controlling a medical procedure. In the illustrated example, the session 500 is enabled by the following hardware components: physician input console 416, physician-side gateway 419, patient-side gateway 429, and robot 422 (see FIG. 4).

Figure 5:
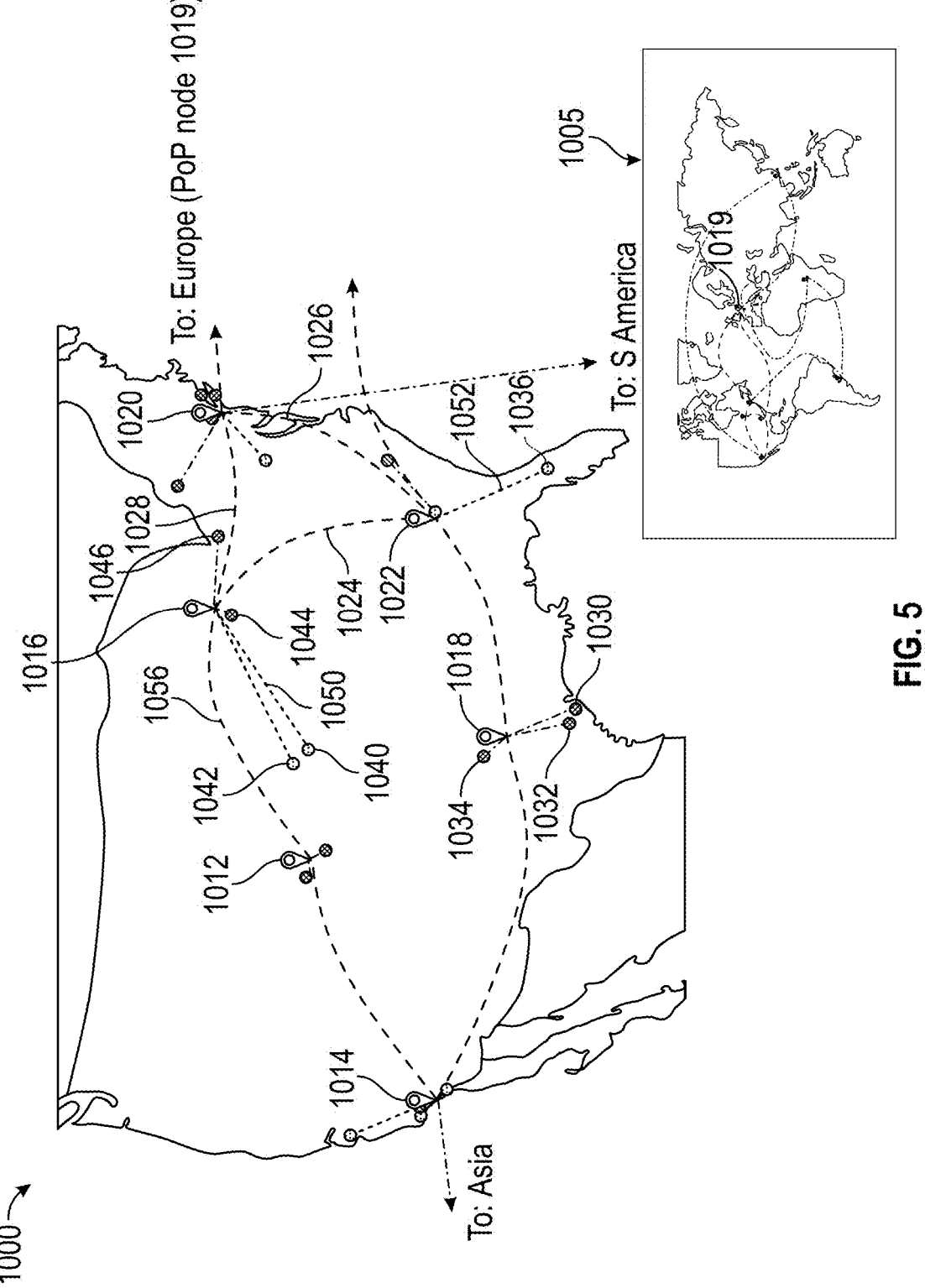
FIG. 5 illustrates a network for remotely controlling robotic procedures.
Figure 9A:
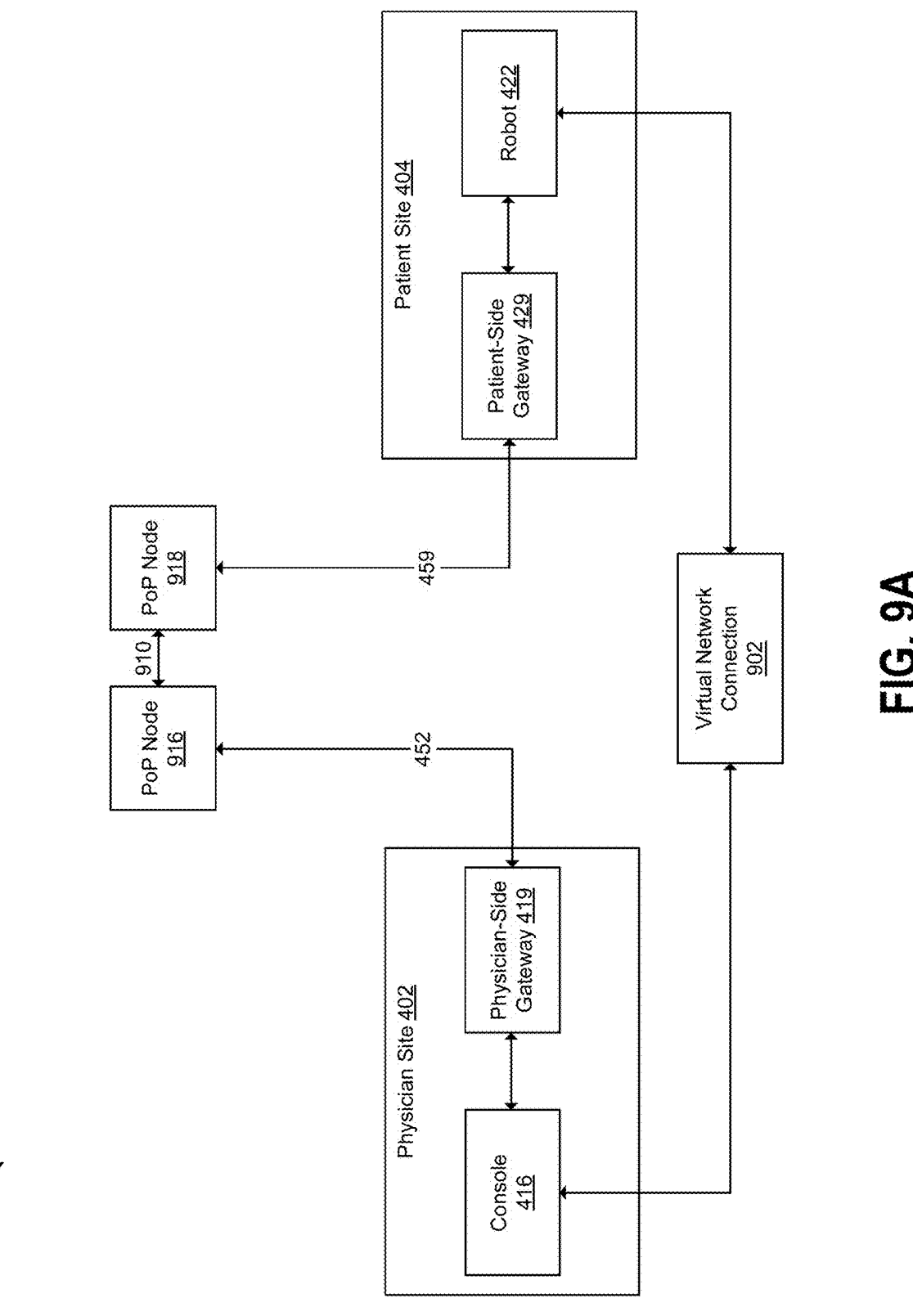
FIGS. 9A-9C illustrate examples of using network virtualization for remotely controlled medical procedures.
Figure 9B:
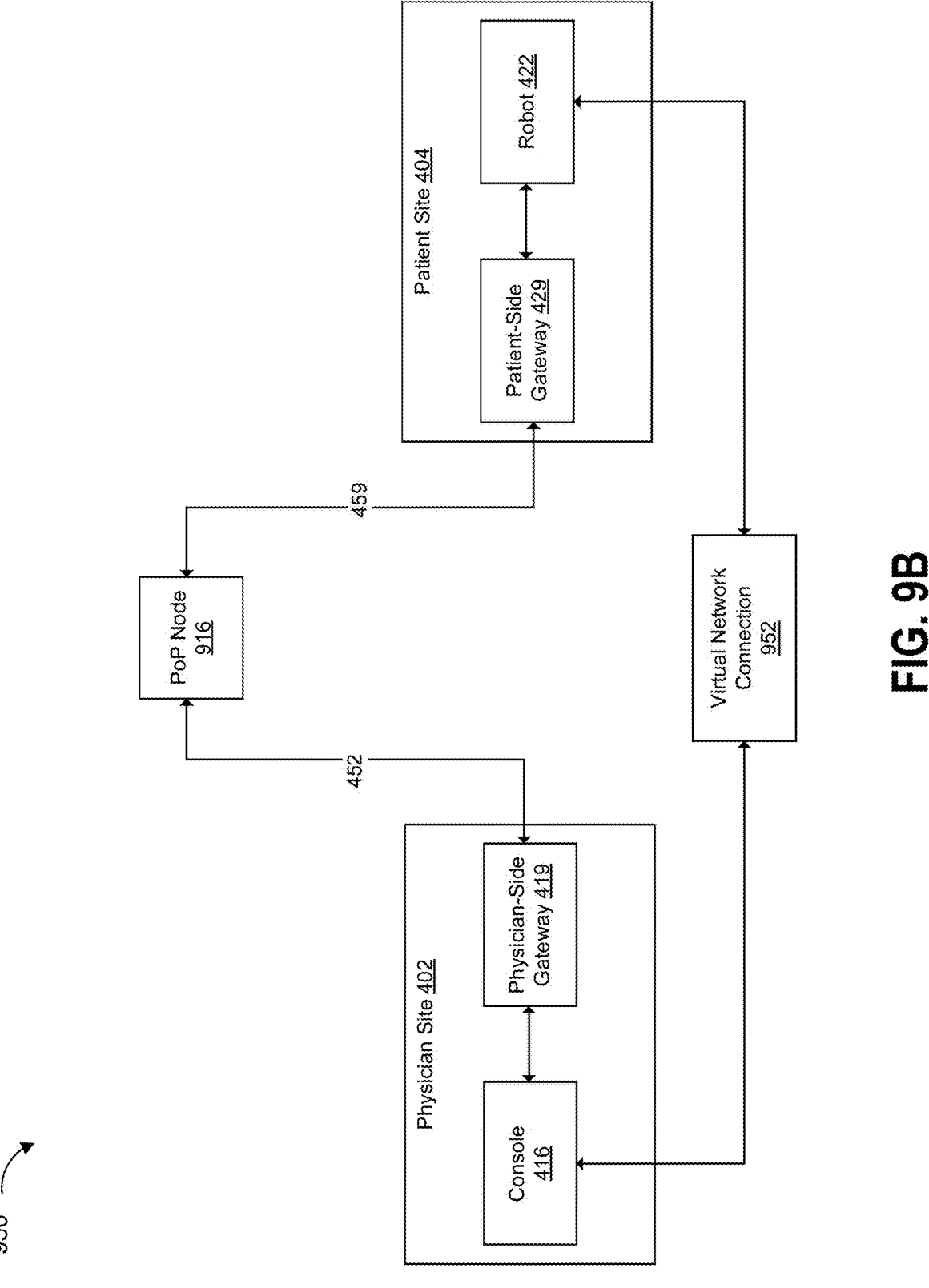

The session 500 can be established and torn down by the network management system 435. Establishing the session 500 can include forming a virtual network connection 502 (sometimes referred to as an overlay). The virtual network connection 502 can span or traverse various different and disparate network connections. With reference to FIGS. 5 and 9A-9B, the virtual network connection 502 can traverse a last mile connection connecting a first site where the console 416 is located to a corresponding first POP node, a last mile connection connecting a second site where the robot 422 is located to a corresponding second POP node, and one or more backbone connections connecting the first and second PoP nodes. The virtual network connection 502 can also traverse local networks at the first and second sites. The virtual network can provide authentication for security, encapsulation to facilitate transmission of data across different and disparate networks (see, for instance, FIG. 7), encryption for secure transmission, separation of data transmission for different sessions (even where data for different sessions is transmitted over at least one overlapping physical network), routing of encapsulated data to the destination, and decapsulation at the destination to obtain transmitted data.

The virtual network connection 502 can provide routing functionality that facilitates moving of data packets across different networks. The virtual network connection 502 can operate at Layer 3 or Layer 4 (which supports sessions control as well as TCP and UDP protocols). In some instances, the virtual network connection 502 is formed using virtual extensible LAN (VXLAN).

The use of the virtual network connection 502 can allow for data to be transmitted across different and disparate networks while blocking unauthorized access to the data. As such, the virtual network connection 502 acts as an encrypted link.

In some implementations, during formation of the virtual network connection 502, statically or dynamically assigned IP addresses of the robot 422 and the console 416 are used. As is explained in more detail herein, encapsulation and decapsulation provided by the virtual network allows the use of such IP addresses without the need for the robot 422 and console 416 to adjust their design that assumes communicating over a direct LAN to communicating over different and disparate network connections. That is, the robot 422 and console 416 can continue to use statically or dynamically assigned IP addresses to transmit data to one another and the data will be correctly and securely routed to the destination.

While illustrated as a point-to-point connection, the virtual network connection 502 can be a multipoint connection, such as between multiple consoles and a single robot.

Suppose that the virtual network connection 502 is formed using VXLAN. Such network connection can be created between the physician-side gateway 419 and the patient-side gateway 429 that can act as VXLAN endpoints (VTEP). For example, the physician-side gateway 419, acting as a source VTEP, can encapsulate network packets to send to the patient-side gateway 429, acting as a destination VTEP, which will decapsulate the network packets to access data transmitted by the console 416. Transmission of data from the robot 422 to the console 416 can be performed similarly with the roles of source and destination VTEPs reversed.

Figure 7:
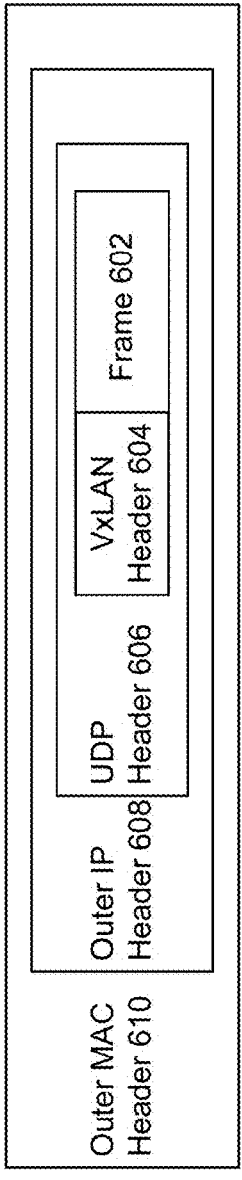
FIG. 7 is an example data packet format suitable for network virtualization.

FIG. 7 illustrates a schematic view of a network packet 600 configured to be sent over the virtual network connection 502 (such as using VXLAN). To encapsulate a frame 602 (such as an Ethernet frame) to be transmitted using VXLAN, a source VTEP can add additional header information to the network packet 600, as described below. The frame 602 includes payload data, such as control signals or image data, as well as the address of the console or robot (such as an IP address).

In the illustrated example, a VXLAN header 604 in the network packet 600 uniquely identifies the particular virtual network connection (such as the virtual network connection 502). The VXLAN header 604 contains a VXLAN network identifier (VNI). The VNI may be unique for each VXLAN and allow the VXLAN to be identified by each participating network. The size of VNI can be large to support sufficient number of virtual network connections (such as 24 bits to support over 16 million virtual networks connection) and to provide scalability.

In the illustrated example, a UDP header 606 in the network packet 600 allows the network packet to be transmitted across the physical network (such as the network 1000) to a destination VTEP. The UDP header 606 may contain source and destination VTEP information, such as port information. The UDP header 606 can be strategically placed within the network packet 600 to keep the Layer 2 networking protocols outer MAC header 610 and VXLAN header 604 from the Layer 3 networking protocols IP header 608 and UDP header 606.

In the illustrated example, an outer IP header 608 contains the IP address of the source and destination VTEPs. The IP header 608 allows the network packet 600 to be properly routed.

In the illustrated example, the outer MAC header 610 contains the MAC address of the next-hop device and the MAC address of the source VTEP. The MAC address of the next-hop device is updated at each network hop as the network packet 600 moves through the network to ensure that the network packet 600 is correctly forwarded across the network. The outer MAC header 610 facilitates forwarding of the network packet 600 using VXLAN.

When the network packet 600 is received at the destination VTEP, it is decapsulated and the payload is forwarded to the destination device (robot or physician console). The structure of the network packet 600 allows forwarding payload across multiple different and disparate networks.

Figure 8:
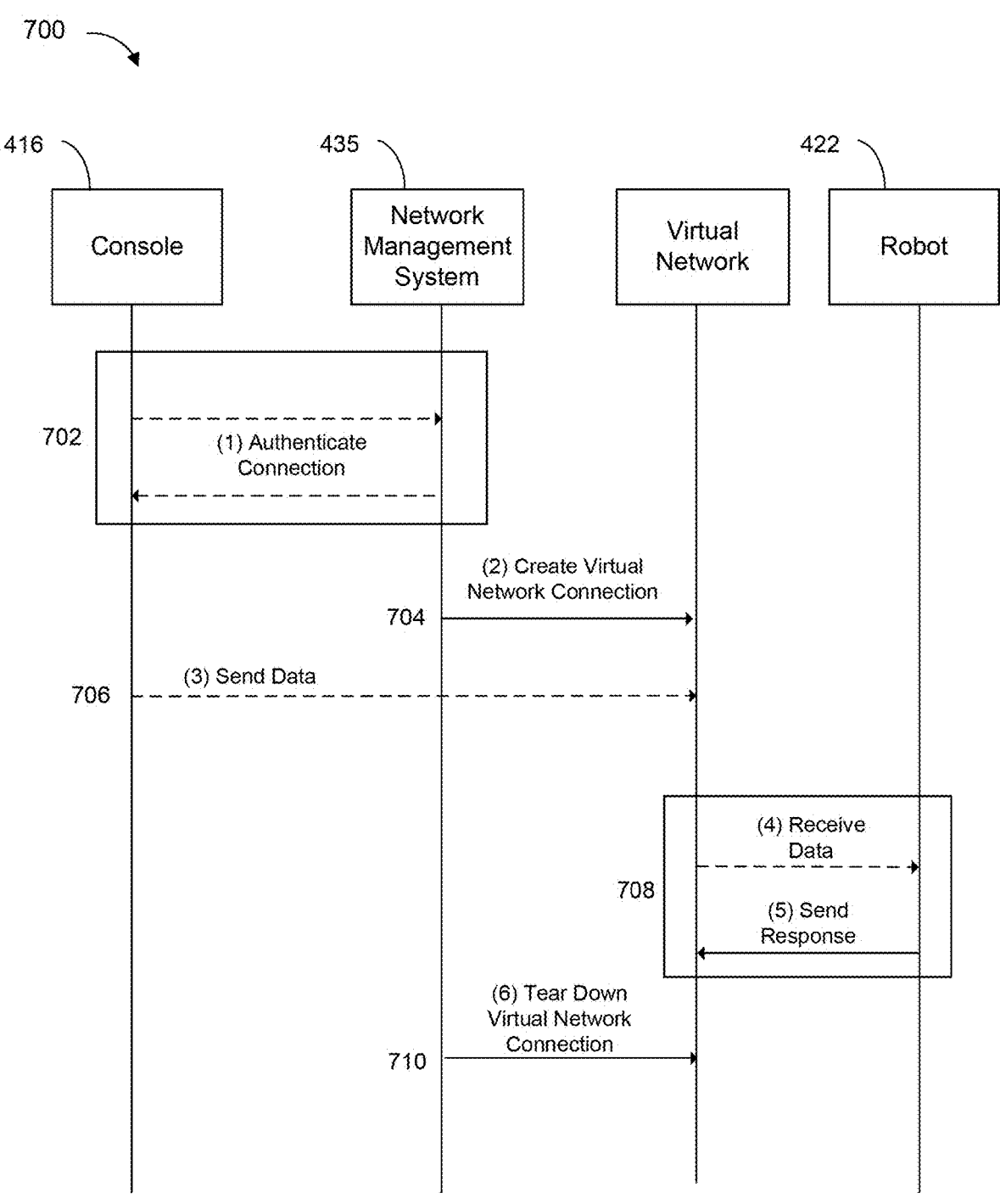
FIG. 8 illustrates a process of using network virtualization for remotely controlled robotic procedures.

FIG. 8 illustrates an example of a process 700 for performing a remotely controlled medical procedure using network virtualization. The process 700 includes a series of communications between one or more of the physician input console 416 (and/or the physician-side gateway 419), the network management system 435, and the robot 422 (and/or the patient-side gateway 429). The process 700 can be performed by the virtual network, which can be at least partially implemented by the network management system 435).

In the illustrated example, initialization at 702 involves one or more communications between the physician input console 416 and network management system 435 to establish a virtual network connection. Initialization can be performed after a procedure has been scheduled. The physician input console 416 may send a connection request to connect to the robot 422 to the network management system 435. Once the physician input console 416 has been authenticated for connection to the robot 422, the network management system 435 can establish at 704 the virtual network connection, as described herein. Both the physician input console 416 and robot 422 can be authenticated at 702. Authentication can involve ensuring the only authorized consoles and robots are connected by a virtual network connection. As described herein, establishing the virtual network connection can include verifying compatibility of the console and robot.

Once the virtual network connection has been established, it can remain functional or active until it has been torn down (such as after the procedure ends). In some cases, the virtual network connection can remain active for a duration of time after the procedure has ended to allow for possible reconnection of the input console.

In some cases, successful authentication provides network information (such as physical ports, MAC addresses, etc.) for establishing VXLAN. For instance, authentication can involve using 802.1x authentication for port-based security and access control. In some cases, authentication can be performed at Layer 2. Network information learned during authentication can be leveraged to efficiently create the virtual network connection.

Virtual network connections can be dynamically created as needed. In some implementations, the virtual network can be scaled to handle, for instance over 16 million simultaneous virtual network connections.

In the illustrated example, after the virtual network connection has been established, data can be securely transmitted between the physician input console and robot 422, as is shown at the 706 step of the process 700. As is described herein, data can be encapsulated and transmitted. Communication can be encrypted and separated from other communications that may use the same physical network(s). As a result, virtual network connections connecting different consoles and robots remain independent and separate. Using the virtual network connection, even though the physician input console 416 and robot 422 may be located far apart and connected by different or disparate networks, they can interact as if they were connected by a direct LAN.

For example, suppose that robot A and robot B located at the same robotic procedure site are used for performing medical procedures A and B by remotely located physicians operating consoles A and B, respectively, located at the same physician site. Suppose further that procedures A and B overlap temporally. Virtual network connections connecting console A to robot A and console B to robot B remain independent and separate despite sharing at least the physical networks at the robotic procedure and physician sites (as well as the onramp connections and, in some instances, one or more backbone connections). Procedures A and B can overlap in time and be initiated or terminated at same or different times (for instance, procedure A can be initiated before procedure B and terminated before procedure B).

As is described herein, robots A and B can be connected to a patient-side gateway located at the patient site by dedicated network connections (such as, via a dedicated Ethernet cables plugged into different ports in the patient-side gateway). Because these dedicated network connections are made to the patient-side gateway, they can be referred to as sharing the same physical network at the patient site. Consoles A and B can be similarly connected to a physician-side gateway and can similarly share the same physical network at the physician side.

As another example, suppose that robots A and B are located at different robotic procedure sites and consoles A and B are located at different physician sites. Virtual network connections connecting console A to robot A and console B to robot B remain independent and separate despite sharing, for instance, one or more backbone connections.

In some examples, there is one physician input console 416 connected to the robot 422 during the medical procedure. In other examples, there can be multiple physician input consoles 416 connected to the same robot 422 during the medical procedure, which can be advantageous for training and collaboration. In such example, the process 700 can be executed for each such physician input console 416.

Continuing with the above example, suppose that two physician input consoles 416 are connected to the same robot 422 located remotely from the multiple physician input consoles. Two physician input consoles can be connected to a physician-side gateway by sharing the same physical network at a physician site (such as, the same LAN connection). Because the consoles share the same physical network connection, they can be referred to as sharing the same physical network at the physician site. Alternatively, two physician input consoles can be connected to the physician-side gateway by two dedicated network connections, which can also be referred to as sharing the same physical network at the physician site as described herein.

In the illustrated example, at 708, the robot 422 receives data transmitted over the virtual network connection. As described herein, data can be received and decapsulated. The robot 422 can send one or more of response data (such as one or more acknowledgments) or image data to the physician input console 416 over the virtual network connection. Response data can be encapsulated as described herein.

The physician input console 416 and robot 422 can perform 706 and 708 until the medical procedure is complete. Once the procedure has been completed, the virtual network connection can be torn down at 710, effectively terminating the connection between the physician input console 416 and the robot 422. The connection can be torn down by the network management system 435. For instance, the connection can be torn down after a session for performing the medical procedure has been completed.

FIG. 9A illustrates a block diagram 900 of establishing a virtual network connection between a physician input console 416 located at a physician site 402 and a robot 422 located at a patient site 404 for performing a remote medical procedure. The console may be connected to a physician-side gateway 419, which can be connected to a POP node 916 by a last mile connection 452. The robot may be connected to a patient-side gateway 429, which can be connected to a POP node 918 by a last mile connection 459. The first POP node and second POP node may be connected via a backbone connection 910 as described herein (such as, with respect to FIG. 5).

As described herein, a virtual network connection 902 can be established for connecting the physician input console 416 and the robot 422. As is illustrated in the block diagram 900, the virtual network connection 902 (such as VxLAN) can be established to connect the physician input console 416 connected to the POP node 916 to the robot 422 connected to a different POP node (POP node 918). The virtual network connection 902 (which can utilize VXLAN) can be established using the gateways 419 and 429. By establishing the virtual network connection 902, a secure and encapsulated connection between the physician input console 416 and the robot 422 can be provided. The virtual network connection 902 can enable the physician input console 416 to facilitate the transmission of encapsulated, encrypted data across the disparate physical networks (such as, the physician site, last mile connection 452, backbone connection 910, last mile connection 459, and patient site 404) to the robot 422. The patient-side gateway 429 alone or in combination with the robot 422 can decapsulate and decrypt the data to obtain the transmitted data. In some instances, the same procedure is utilized to transmit data (such as image data or status data) from the robot 422 to the physician input console 416. After the medical procedure has been completed, the virtual network connection 902 can be torn down, as described herein. Subsequently, a different virtual network connection can be established between the physician input console 416 and another robot 422 that may be located in the same patient site 404 or in a different patient site 404.

FIG. 9B illustrates a block diagram 950 of establishing a virtual network connection 952 between the physician site 402 and the patient site 404 for performing a remote medical procedure. The block diagram 950 is similar to the block diagram 900 with the exception of a single PoP node 916 being traversed.

Figure 9C:
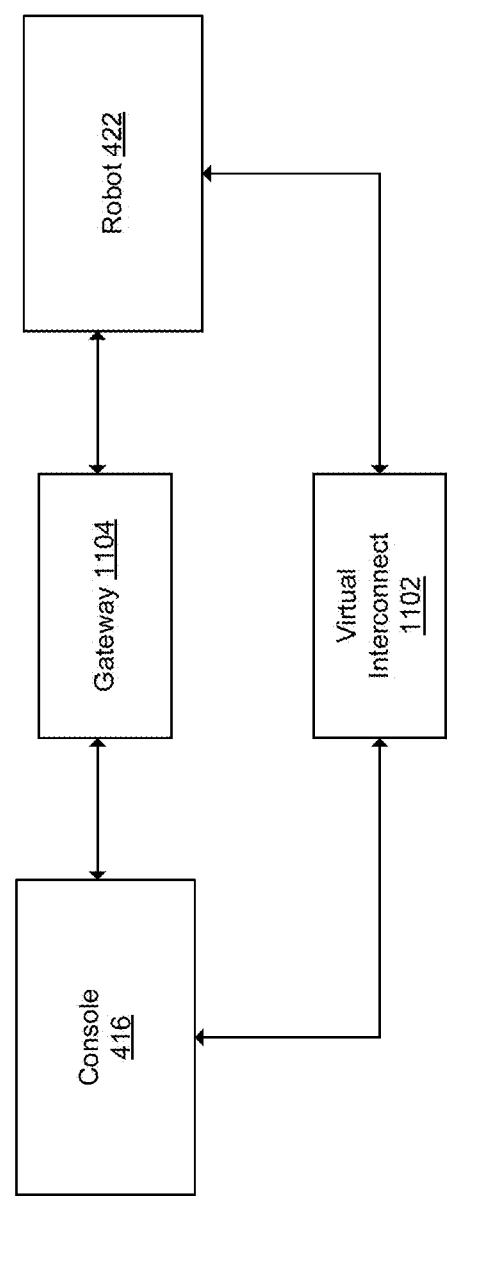

FIG. 9C illustrates a block diagram 980 of establishing a virtual interconnect 1102 between the physician input console 416 and the robot 422 for performing a medical procedure. The physician input console 416 and the robot 422 are connected to the same gateway 1104. In the illustrated example, the physician input console 416 and the robot 422 can be located in the same site, such as in the same medical center. No POP nodes would be needed to connect the physician input console 416 and the robot 422.

The physician input console 416 and the robot 422 can by connected to different network switches and can be on different virtual area local networks (VLANs). Because the physician input console 416 and the robot are in the same physical location where they are behind the same gateway (or router/firewall), it may not be possible to utilize VXLAN to connect the different VLANs at Layer 3, which provides routing functionality. Instead, the virtual interconnect 1102 between the two VLANs can be formed to allow the physician input console and robot pair to communicate. Unlike VXLAN which can operate at Layer 3 (or Layer 4), the virtual interconnect 1102 may only operate at Layer 2, which provides switching functionality but not routing functionality. The virtual interconnect can be a software switch. Using the virtual interconnect 1102 can be done in lieu of using a virtual network connection (such as by using VxLAN) since forming the virtual network connection would necessitate that the physician console and robot be behind two separate gateways, which typically occurs when they are positioned into two different physical locations.

Other Variations

Any of the approaches described herein can utilize any of the examples disclosed in U.S. Pat. Nos. 12,089,906, 12,064,202, U.S. patent application Ser. No. 19/191,839 filed on Apr. 28, 2025, U.S. patent application Ser. No. 19/273,503 filed on Jul. 18, 2025, U.S. patent application Ser. No. 19/273,545 filed on Jul. 18, 2025, and U.S. patent application Ser. No. 19/273,589 filed on Jul. 18, 2025, each of is incorporated by reference in its entirety.

While displaying has been used to describe certain examples of outputting information, any type of visual, auditory, or tactile output can be performed in addition to or alternatively.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, implementation, or example are to be understood to be applicable to any other aspect, implementation, or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some cases, the actual steps taken in the processes illustrated and/or disclosed may differ from those shown in the figures. Depending on the implementation, certain of the steps described above may be removed, others may be added. For example, the actual steps and/or order of steps taken in the disclosed processes may differ from those shown in the figure. Various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific examples disclosed above may be combined in different ways to form additional implementations, all of which fall within the scope of the present disclosure.

Conditional language used herein, such as, among others, "can," "could", "might," "may," "e.g.," and the like, unless specifically stated otherwise, or otherwise understood within the context as used, is generally intended to convey that certain implementation include, while other implementations do not include, certain features, elements and/or states. Thus, such conditional language is not generally intended to imply that features, elements and/or states are in any way required for one or more implementations or that one or more implementations necessarily include logic for deciding, with or without author input or prompting, whether these features, elements and/or states are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain implementations require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While specific implementations have been described and illustrated, such implementations should be considered illustrative only and not as limiting. Accordingly, the scope of the present disclosure is not intended to be limited by the specific disclosures of preferred implementations herein, and may be defined by claims as presented herein or as presented in the future.

Example Implementations

The following provides example systems, methods, and computer-readable media for remotely controlling robotic-assisted medical systems. The examples are not intended to limit the implementations described herein but are intended to illustrate the various implementations. Any of the features from a particular example can be combined with any other one or more features from other one or more examples.

Clause 1. A robotic-assisted medical procedure system comprising: a plurality of patient-side robotic procedure systems including a first patient-side robotic procedure system and a second patient-side robotic procedure system each comprising at least one of an instrument or an imaging system; a plurality of robotic procedure consoles including a first robotic procedure console and a second robotic procedure console each configured to control a remotely located patient-side robotic procedure system of the plurality of patient-side robotic procedure systems; and a non-transitory computer readable medium storing instructions that, when executed by one or more processors, cause the one or more processors to: provide a virtual network for connecting 1) the first robotic procedure console to the first patient-side robotic procedure system and 2) the second robotic procedure console to the second patient-side robotic procedure system, the virtual network utilizing a plurality of different and disparate physical networks that comprise a first physical network on which the first robotic procedure console is configured to reside, a second physical network on which the second robotic procedure console is configured to reside, a third physical network on which the first patient-side robotic procedure system is configured to reside, and a fourth physical network on which the second patient-side robotic procedure system is configured to reside; authenticate the first and second robotic procedure consoles for the virtual network; authenticate the first and second patient-side robotic procedure systems for the virtual network; subsequent to authenticating the first robotic procedure console and the first patient-side robotic procedure system: establish, over the virtual network, a first virtual network connection between the first robotic procedure console and the first patient-side robotic procedure system, the first virtual network connection utilizing the first physical network, the third physical network, and a backbone network; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system: establish, over the virtual network, a second virtual network connection between the second robotic procedure console and the second patient-side robotic procedure system, the second virtual network connection utilizing the second physical network, the fourth physical network, and the backbone network; and transmit, over the second virtual network connection, data between the second robotic procedure console and the second patient-side robotic procedure system to permit the second robotic procedure console to remotely control the second patient-side robotic procedure system to perform a second medical procedure, the second medical procedure overlapping in time with the first medical procedure, wherein the first and second virtual network connections remain independent and separate despite sharing at least the backbone network.

Clause 2. The robotic-assisted medical procedure system of clause 1, wherein the first and second virtual network connections provide routing functionality.

Clause 3. The robotic-assisted medical procedure system of clause 2, wherein the plurality of patient-side robotic procedure systems further comprises a third patient-side robotic procedure system that is configured to reside on the first physical network on which the first robotic procedure console is configured to reside, and wherein the one or more processors are further caused to: authenticate the third patient-side robotic procedure system for the virtual network; and subsequent to authenticating the first robotic procedure console and the third patient-side robotic procedure system: establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

Clause 4. The robotic-assisted medical procedure system of any one of clauses 1 to 3, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 5. The robotic-assisted medical procedure system of clause 4, wherein the first IP address assigned to the first patient-side robotic procedure system is a first hard-coded IP address.

Clause 6. The robotic-assisted medical procedure system of clause 5, wherein the first hard-coded IP address of the first patient-side robotic procedure system overlaps with a hard-coded IP address of another patient-side robotic procedure system of the plurality of patient-side robotic procedure systems.

Clause 7. The robotic-assisted medical procedure system of any one of clauses 4 to 6, wherein the first IP address assigned to the first patient-side robotic procedure system is dynamically assigned.

Clause 8. The robotic-assisted medical procedure system of any one of clauses 4 to 7, wherein the first IP address is an address on a local area network designed to directly connect the first patient-side robotic procedure system to the first robotic procedure console.

Clause 9. The robotic-assisted medical procedure system of any one of clauses 4 to 8, wherein: the second robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks.

Clause 10. The robotic-assisted medical procedure system of clause 9, wherein the second IP address is an address on a local area network designed to directly connect the second patient-side robotic procedure system to the second robotic procedure console.

Clause 11. A non-transitory computer readable medium storing instructions that, when executed by one or more processors, cause the one or more processors to: provide a virtual network for connecting: a first robotic procedure console of a plurality of robotic procedure consoles to a first patient-side robotic procedure system of a plurality of patient-side robotic procedure systems, the first patient-side robotic procedure system configured to be remotely located from the first robotic procedure console; and a second robotic procedure console of the plurality of robotic procedure consoles to a second patient-side robotic procedure system of the plurality of patient-side robotic procedure systems, the second patient-side robotic procedure system configured to be remotely located from the second robotic procedure console, the virtual network utilizing a plurality of different and disparate physical networks that comprise a first physical network on which the first robotic procedure console is configured to reside, a second physical network on which the second robotic procedure console is configured to reside, a third physical network on which the first patient-side robotic procedure system is configured to reside, and a fourth physical network on which the second patient-side robotic procedure system is configured to reside; authenticate the first and second robotic procedure consoles for the virtual network; authenticate the first and second patient-side robotic procedure systems for the virtual network; subsequent to authenticating the first robotic procedure console and the first patient-side robotic procedure system: establish, over the virtual network, a first virtual network connection between the first robotic procedure console and the first patient-side robotic procedure system, the first virtual network connection utilizing the first physical network, the third physical network, and a backbone network; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system: establish, over the virtual network, a second virtual network connection between the second robotic procedure console and the second patient-side robotic procedure system, the second virtual network connection utilizing the second physical network, the fourth physical network, and the backbone network; and transmit, over the second virtual network connection, data between the second robotic procedure console and the second patient-side robotic procedure system to permit the second robotic procedure console to remotely control the second patient-side robotic procedure system to perform a second medical procedure, the second medical procedure overlapping in time with the first medical procedure, wherein the first and second virtual network connections remain independent and separate despite sharing at least the backbone network.

Clause 12. The non-transitory computer readable medium of clause 11, wherein the first and second virtual network connections provide routing functionality.

Clause 13. The non-transitory computer readable medium of clause 12, wherein the one or more processors are further caused to: authenticate a third patient-side robotic procedure system for the virtual network, the third patient-side robotic procedure system configured to reside on the first physical network on which the first robotic procedure console is configured to reside; and subsequent to authenticating the first robotic procedure console and the third patient-side robotic procedure system: establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

Clause 14. The non-transitory computer readable medium of any one of clauses 11 to 13, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 15. The non-transitory computer readable medium of clause 14, wherein the first IP address assigned to the first patient-side robotic procedure system is a first hard-coded IP address.

Clause 16. The non-transitory computer readable medium of clause 15, wherein the first hard-coded IP address of the first patient-side robotic procedure system overlaps with a hard-coded IP address of another patient-side robotic procedure system of the plurality of patient-side robotic procedure systems.

Clause 17. The non-transitory computer readable medium of any one of clauses 14 to 16, wherein the first IP address assigned to the first patient-side robotic procedure system is dynamically assigned.

Clause 18. The non-transitory computer readable medium of any one of clauses 14 to 17, wherein the first IP address is an address on a local area network designed to directly connect the first patient-side robotic procedure system to the first robotic procedure console.

Clause 19. The non-transitory computer readable medium of any one of clauses 14 to 18, wherein: the second robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks.

Clause 20. The non-transitory computer readable medium of clause 19, wherein the second IP address is an address on a local area network designed to directly connect the second patient-side robotic procedure system to the second robotic procedure console.

Clause 21. A robotic-assisted medical procedure system comprising: a plurality of patient-side robotic procedure systems including a first patient-side robotic procedure system and a second patient-side robotic procedure system each comprising at least one of an instrument or an imaging system; a robotic procedure console configured to control the plurality of patient-side robotic procedure systems located remotely from the robotic procedure console; and a non-transitory computer readable medium storing instructions that, when executed by one or more processors, cause the one or more processors to: provide a virtual network for connecting the robotic procedure console to the first and second patient-side robotic procedure systems, the virtual network utilizing a plurality of different and disparate physical networks that comprise a first physical network on which the robotic procedure console is configured to reside and a second physical network on which the first and second patient-side robotic procedure systems are configured to reside; authenticate the robotic procedure console for the virtual network; authenticate the first and second patient-side robotic procedure systems for the virtual network; subsequent to authenticating the robotic procedure console and at least the first patient-side robotic procedure system: establish, over the virtual network, a first virtual network connection between the robotic procedure console and the first patient-side robotic procedure system; transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure; and subsequent to completion of the first medical procedure: establish, over the virtual network, a second virtual network connection between the robotic procedure console and the second patient-side robotic procedure system; transmit, over the second virtual network connection, data between the robotic procedure console and the second patient-side robotic procedure system to permit the robotic procedure console to remotely control the second patient-side robotic procedure system to perform a second medical procedure; and terminate the second virtual network connection subsequent to completion of the second medical procedure, wherein each of the first and second virtual network connections remain independent and separate from any other temporally overlapping virtual network connection that shares at least one physical network with the first or second virtual network connection.

Clause 22. The robotic-assisted medical procedure system of clause 21, wherein the first and second virtual network connections provide routing functionality.

Clause 23. The robotic-assisted medical procedure system of clause 22, wherein the plurality of patient-side robotic procedure systems further comprises a third patient-side robotic procedure system that is configured to reside on the first physical network on which the robotic procedure console is configured to reside, and wherein the one or more processors are further caused to: authenticate the third patient-side robotic procedure system for the virtual network; and subsequent to authenticating the robotic procedure console and the third patient-side robotic procedure system: establish, over the virtual network, a virtual interconnect between the robotic procedure console and the third patient-side robotic procedure system, wherein the virtual interconnect provides switching functionality and does not provide routing functionality; transmit, over the virtual interconnect, data between the robotic procedure console and the third patient-side robotic procedure system to permit the robotic procedure console to control the third patient-side robotic procedure system to perform a third medical procedure, wherein the third medical procedure does not overlap in time with the first or second medical procedure; and terminate the virtual interconnect subsequent to completion of the third medical procedure.

Clause 24. The robotic-assisted medical procedure system of any one clauses 21 to 23, wherein the robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 25. The robotic-assisted medical procedure system of clause 24, wherein the first IP address assigned to the first patient-side robotic procedure system is a first hard-coded IP address.

Clause 26. The robotic-assisted medical procedure system of clause 25, wherein the first hard-coded IP address of the first patient-side robotic procedure system overlaps with a hard-coded IP address of another patient-side robotic procedure system of the plurality of patient-side robotic procedure systems.

Clause 27. The robotic-assisted medical procedure system of any one clauses 24 to 26, wherein the first IP address assigned to the first patient-side robotic procedure system is dynamically assigned.

Clause 28. The robotic-assisted medical procedure system of any one of clauses 24 to 27, wherein the first IP address is an address on a local area network designed to directly connect the first patient-side robotic procedure system to the robotic procedure console.

Clause 29. The robotic-assisted medical procedure system of any one of clauses 24 to 28, wherein: the robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks.

Clause 30. The robotic-assisted medical procedure system of clause 29, wherein the second IP address is an address on a local area network designed to directly connect the second patient-side robotic procedure system to the robotic procedure console.

Clause 31. A non-transitory computer readable medium storing instructions that, when executed by one or more processors, cause the one or more processors to: provide a virtual network for connecting a robotic procedure console to first and second patient-side robotic procedure systems of a plurality of patient-side robotic procedure systems, the virtual network utilizing a plurality of different and disparate physical networks that comprise a first physical network on which the robotic procedure console is configured to reside and a second physical network on which the first and second patient-side robotic procedure systems are configured to reside; authenticate the robotic procedure console for the virtual network; authenticate the first and second patient-side robotic procedure systems for the virtual network; subsequent to authenticating the robotic procedure console and at least the first patient-side robotic procedure system: establish, over the virtual network, a first virtual network connection between the robotic procedure console and the first patient-side robotic procedure system; transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure; and subsequent to completion of the first medical procedure: establish, over the virtual network, a second virtual network connection between the robotic procedure console and the second patient-side robotic procedure system; transmit, over the second virtual network connection, data between the robotic procedure console and the second patient-side robotic procedure system to permit the robotic procedure console to remotely control the second patient-side robotic procedure system to perform a second medical procedure; and terminate the second virtual network connection subsequent to completion of the second medical procedure, wherein each of the first and second virtual network connections remain independent and separate from any other temporally overlapping virtual network connection that shares at least one physical network with the first or second virtual network connection.

Clause 32. The non-transitory computer readable medium of clause 31, wherein the first and second virtual network connections provide routing functionality.

Clause 33. The non-transitory computer readable medium of clause 32, wherein the one or more processors are further caused to: authenticate a third patient-side robotic procedure system for the virtual network, the third patient-side robotic procedure system is configured to reside on the first physical network on which the robotic procedure console is configured to reside; and subsequent to authenticating the robotic procedure console and the third patient-side robotic procedure system: establish, over the virtual network, a virtual interconnect between the robotic procedure console and the third patient-side robotic procedure system, wherein the virtual interconnect provides switching functionality and does not provide routing functionality; transmit, over the virtual interconnect, data between the robotic procedure console and the third patient-side robotic procedure system to permit the robotic procedure console to control the third patient-side robotic procedure system to perform a third medical procedure, wherein the third medical procedure does not overlap in time with the first or second medical procedure; and terminate the virtual interconnect subsequent to completion of the third medical procedure.

Clause 34. The non-transitory computer readable medium of any one of clauses 31 to 33, wherein the robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 35. The non-transitory computer readable medium of clause 34, wherein the first IP address assigned to the first patient-side robotic procedure system is a first hard-coded IP address.

Clause 36. The non-transitory computer readable medium of clause 35, wherein the first hard-coded IP address of the first patient-side robotic procedure system overlaps with a hard-coded IP address of another patient-side robotic procedure system of the plurality of patient-side robotic procedure systems.

Clause 37. The non-transitory computer readable medium of any one of clauses 34 to 36, wherein the first IP address assigned to the first patient-side robotic procedure system is dynamically assigned.

Clause 38. The non-transitory computer readable medium of any one of clauses 34 to 37, wherein the first IP address is an address on a local area network designed to directly connect the first patient-side robotic procedure system to the robotic procedure console.

Clause 39. The non-transitory computer readable medium of any one of clauses 34 to 38, wherein: the robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks.

Clause 40. The non-transitory computer readable medium of clause 39, wherein the second IP address is an address on a local area network designed to directly connect the second patient-side robotic procedure system to the robotic procedure console.

Clause 41. A robotic-assisted medical procedure system comprising: a plurality of patient-side robotic procedure systems including a first patient-side robotic procedure system and second patient-side robotic procedure system each comprising at least one of an instrument or an imaging system; a plurality of robotic procedure consoles configured to control the plurality of patient-side robotic procedure systems, the plurality of robotic procedure consoles including a first robotic procedure console and a second robotic procedure console; and a non-transitory computer readable medium storing instructions that, when executed by one or more processors, cause the one or more processors to: provide a virtual network for connecting 1) the first robotic procedure console to the first patient-side robotic procedure system and 2) the second robotic procedure console to the second patient-side robotic procedure system, the virtual network utilizing a plurality of different and disparate physical networks that comprise a first physical network on which the first and second robotic procedure consoles are configured to reside and a second physical network on which the first and second patient-side robotic procedure systems are configured to reside; authenticate the first and second robotic procedure consoles for the virtual network; authenticate the first and second patient-side robotic procedure systems for the virtual network; subsequent to authenticating the first robotic procedure console and the first patient-side robotic procedure system: establish, over the virtual network, a first virtual network connection between the first robotic procedure console and the first patient-side robotic procedure system; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system: establish, over the virtual network, a second virtual network connection between the second robotic procedure console and the second patient-side robotic procedure system; and transmit, over the second virtual network connection, data between the second robotic procedure console and the second patient-side robotic procedure system to permit the second robotic procedure console to remotely control the second patient-side robotic procedure system to perform a second medical procedure that overlaps in time with the first medical procedure, wherein the first and second virtual network connections remain independent and separate despite sharing the first and second physical networks.

Clause 42. The robotic-assisted medical procedure system of clause 41, wherein the instructions further cause the one or more processors to: subsequent to completion of the first medical procedure, terminate the first virtual network connection thereby ceasing transmission of data between the first robotic procedure console and the first patient-side robotic procedure system; and prior to completion of the second medical procedure, continue transmission of data between the second robotic procedure console and the second patient-side robotic procedure system using the second virtual network connection.

Clause 43. The robotic-assisted medical procedure system of any one clauses 41 to 42, wherein the instructions further cause the one or more processors to: subsequent to completion of the second medical procedure, terminate the second virtual network connection thereby ceasing transmission of data between the second robotic procedure console and the second patient-side robotic procedure system.

Clause 44. The robotic-assisted medical procedure system of any one of clauses 41 to 43, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 45. The robotic-assisted medical procedure system of clause 44, wherein the first IP address assigned to the first patient-side robotic procedure system is a first hard-coded IP address.

Clause 46. The robotic-assisted medical procedure system of clause 45, wherein the first hard-coded IP address of the first patient-side robotic procedure system overlaps with a hard-coded IP address of another patient-side robotic procedure system of the plurality of patient-side robotic procedure systems.

Clause 47. The robotic-assisted medical procedure system of any one of clauses 44 to 46, wherein the first IP address assigned to the first patient-side robotic procedure system is dynamically assigned.

Clause 48. The robotic-assisted medical procedure system of any one of clauses 44 to 47, wherein the first IP address is an address on a local area network designed to directly connect the first patient-side robotic procedure system to the first robotic procedure console.

Clause 49. The robotic-assisted medical procedure system of any one of clauses 44 to 48, wherein: the second robotic procedure console utilizes a second IP address assigned to the second patient-side robotic procedure system to communicate with the second patient-side robotic procedure system, and the second IP address is automatically encapsulated to facilitate communication with the second patient-side robotic procedure system over the second virtual network connection that traverses multiple local area networks.

Clause 50. The robotic-assisted medical procedure system of clause 49, wherein the second IP address is an address on a local area network designed to directly connect the second patient-side robotic procedure system to the second robotic procedure console.

Clause 51. The robotic-assisted medical procedure system of any one of clauses 41 to 51, wherein the first and second virtual network connections provide routing functionality.

Clause 52. The robotic-assisted medical procedure system of clause 51, wherein the plurality of patient-side robotic procedure systems further comprises a third patient-side robotic procedure system that is configured to reside on the first physical network on which the first robotic procedure console is configured to reside, and wherein the one or more processors are further caused to: authenticate the third patient-side robotic procedure system for the virtual network; and subsequent to authenticating the first robotic procedure console and the third patient-side robotic procedure system: establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

Clause 53. A non-transitory computer readable medium storing instructions that, when executed by one or more processors, cause the one or more processors to: provide a virtual network for connecting: a first robotic procedure console of a plurality of robotic procedure consoles to a first patient-side robotic procedure system of a plurality of patient-side robotic procedure systems, the first patient-side robotic procedure system configured to be remotely located from the first robotic procedure console; and a second robotic procedure console of the plurality of robotic procedure consoles to a second patient-side robotic procedure system of the plurality of patient-side robotic procedure systems, the second patient-side robotic procedure system configured to be remotely located from the second robotic procedure console, the virtual network utilizing a plurality of different and disparate physical networks that comprise a first physical network on which the first and second robotic procedure consoles are configured to reside and a second physical network on which the first and second patient-side robotic procedure systems are configured to reside; authenticate the first and second robotic procedure consoles for the virtual network; authenticate the first and second patient-side robotic procedure systems for the virtual network; subsequent to authenticating the first robotic procedure console and the first patient-side robotic procedure system: establish, over the virtual network, a first virtual network connection between the first robotic procedure console and the first patient-side robotic procedure system; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system: establish, over the virtual network, a second virtual network connection between the second robotic procedure console and the second patient-side robotic procedure system; and transmit, over the second virtual network connection, data between the second robotic procedure console and the second patient-side robotic procedure system to permit the second robotic procedure console to remotely control the second patient-side robotic procedure system to perform a second medical procedure that overlaps in time with the first medical procedure, wherein the first and second virtual network connections remain independent and separate despite sharing the first and second physical networks.

Clause 54. The non-transitory computer readable medium of clause 53, wherein the instructions further cause the one or more processors to: subsequent to completion of the first medical procedure, terminate the first virtual network connection thereby ceasing transmission of data between the first robotic procedure console and the first patient-side robotic procedure system; and prior to completion of the second medical procedure, continue transmission of data between the second robotic procedure console and the second patient-side robotic procedure system using the second virtual network connection.

Clause 55. The non-transitory computer readable medium of any one of clauses 53 to 54, wherein the instructions further cause the one or more processors to: subsequent to completion of the second medical procedure, terminate the second virtual network connection thereby ceasing transmission of data between the second robotic procedure console and the second patient-side robotic procedure system.

Clause 56. The non-transitory computer readable medium of any one of clauses 53 to 55, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 57. The non-transitory computer readable medium of clause 56, wherein the first IP address assigned to the first patient-side robotic procedure system is a first hard-coded IP address.

Clause 58. The non-transitory computer readable medium of clause 57, wherein the first hard-coded IP address of the first patient-side robotic procedure system overlaps with a hard-coded IP address of another patient-side robotic procedure system of the plurality of patient-side robotic procedure systems.

Clause 59. The non-transitory computer readable medium of any one of clauses 56 to 58, wherein the first IP address assigned to the first patient-side robotic procedure system is dynamically assigned.

Clause 60. The non-transitory computer readable medium of any one of clauses 56 to 59, wherein the first IP address is an address on a local area network designed to directly connect the first patient-side robotic procedure system to the first robotic procedure console.

Clause 61. The non-transitory computer readable medium of any one of clauses 56 to 60, wherein: the second robotic procedure console utilizes a second IP address assigned to the second patient-side robotic procedure system to communicate with the second patient-side robotic procedure system, and the second IP address is automatically encapsulated to facilitate communication with the second patient-side robotic procedure system over the second virtual network connection that traverses multiple local area networks.

Clause 62. The non-transitory computer readable medium of clause 61, wherein the second IP address is an address on a local area network designed to directly connect the second patient-side robotic procedure system to the second robotic procedure console.

Clause 63. The non-transitory computer readable medium of any one of clauses 53 to 62, wherein the first and second virtual network connections provide routing functionality.

Clause 64. The non-transitory computer readable medium of clause 63, wherein the one or more processors are further caused to: authenticate a third patient-side robotic procedure system for the virtual network, the third patient-side robotic procedure system configured to reside on the first physical network on which the first robotic procedure console is configured to reside; and subsequent to authenticating the first robotic procedure console and the third patient-side robotic procedure system: establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

Clause 65. A robotic-assisted medical procedure system comprising: a plurality of patient-side robotic procedure systems including a first patient-side robotic procedure system comprising at least one of an instrument or an imaging system; a robotic procedure console configured to control a plurality of patient-side robotic procedure systems located remotely from the robotic procedure console; and a non-transitory computer readable medium storing instructions that, when executed by one or more processors, cause the one or more processors to: provide a virtual network for connecting the robotic procedure console to the first patient-side robotic procedure system, the virtual network utilizing a plurality of different and disparate physical networks that comprise a first physical network on which the robotic procedure console is configured to reside and a second physical network on which the first patient-side robotic procedure system is configured to reside; authenticate the robotic procedure console for the virtual network; authenticate the first patient-side robotic procedure system for the virtual network; and subsequent to authenticating the robotic procedure console and the first patient-side robotic procedure system: establish, over the virtual network, a first virtual network connection between the robotic procedure console and the first patient-side robotic procedure system; transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure, wherein the first virtual network connection remains independent and separate from any other temporally overlapping virtual network connection that shares at least one physical network with the first virtual network connection.

Clause 66. The robotic-assisted medical procedure system of clause 65, wherein the first virtual network connection provides routing functionality.

Clause 67. The robotic-assisted medical procedure system of any one of clauses 65 to 66, wherein the plurality of patient-side robotic procedure systems further comprises a second patient-side robotic procedure system that is configured to reside on the first physical network on which the robotic procedure console is configured to reside, and wherein the one or more processors are further caused to: authenticate the second patient-side robotic procedure system for the virtual network; and subsequent to authenticating the robotic procedure console and the second patient-side robotic procedure system: establish, over the virtual network, a virtual interconnect between the robotic procedure console and the second patient-side robotic procedure system, wherein the virtual interconnect provides switching functionality and does not provide routing functionality; and transmit, over the virtual interconnect, data between the robotic procedure console and the second patient-side robotic procedure system to permit the robotic procedure console to control the second patient-side robotic procedure system to perform a second medical procedure, wherein the second medical procedure does not overlap in time with the first medical procedure.

Clause 68. The robotic-assisted medical procedure system of any one of clauses 65 to 67, wherein the robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 69. The robotic-assisted medical procedure system of clause 68, wherein the first IP address assigned to the first patient-side robotic procedure system is a first hard-coded IP address.

Clause 70. The robotic-assisted medical procedure system of clause 69, wherein the first hard-coded IP address of the first patient-side robotic procedure system overlaps with a hard-coded IP address of another patient-side robotic procedure system of the plurality of patient-side robotic procedure systems.

Clause 71. The robotic-assisted medical procedure system of any one of clauses 68 to 70, wherein the first IP address assigned to the first patient-side robotic procedure system is dynamically assigned.

Clause 72. The robotic-assisted medical procedure system of any one of clauses 68 to 71, wherein the first IP address is an address on a local area network designed to directly connect the first patient-side robotic procedure system to the robotic procedure console.

Clause 73. A non-transitory computer readable medium storing instructions that, when executed by one or more processors, cause the one or more processors to: provide a virtual network for connecting a robotic procedure console to a first patient-side robotic procedure system configured to located remotely from the robotic procedure console, the virtual network utilizing a plurality of different and disparate physical networks that comprise a first physical network on which the robotic procedure console is configured to reside and a second physical network on which the first patient-side robotic procedure system is configured to reside; authenticate the robotic procedure console for the virtual network; authenticate the first patient-side robotic procedure system for the virtual network; and subsequent to authenticating the robotic procedure console and the first patient-side robotic procedure system: establish, over the virtual network, a first virtual network connection between the robotic procedure console and the first patient-side robotic procedure system; transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure, wherein the first virtual network connection remains independent and separate from any other temporally overlapping virtual network connection that shares at least one physical network with the first virtual network connection.

Clause 74. The non-transitory computer readable medium of clause 73, wherein the first virtual network connection provides routing functionality.

Clause 75. The non-transitory computer readable medium of clause 74, wherein the one or more processors are further caused to: authenticate a second patient-side robotic procedure system for the virtual network, the second patient-side robotic procedure system that is configured to reside on the first physical network on which the robotic procedure console is configured to reside; and subsequent to authenticating the robotic procedure console and the second patient-side robotic procedure system: establish, over the virtual network, a virtual interconnect between the robotic procedure console and the second patient-side robotic procedure system, wherein the virtual interconnect provides switching functionality and does not provide routing functionality; and transmit, over the virtual interconnect, data between the robotic procedure console and the second patient-side robotic procedure system to permit the robotic procedure console to control the second patient-side robotic procedure system to perform a second medical procedure, wherein the second medical procedure does not overlap in time with the first medical procedure.

Clause 76. The non-transitory computer readable medium of any one of clauses 73 to 75, wherein the robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

Clause 77. The non-transitory computer readable medium of clause 76, wherein the first IP address assigned to the first patient-side robotic procedure system is a first hard-coded IP address.

Clause 78. The non-transitory computer readable medium of any one clause 77, wherein the first hard-coded IP address of the first patient-side robotic procedure system overlaps with a hard-coded IP address of another patient-side robotic procedure system.

Clause 79. The non-transitory computer readable medium of any one of clauses 76 to 78, wherein the first IP address assigned to the first patient-side robotic procedure system is dynamically assigned.

Clause 80. The non-transitory computer readable medium of any one of clauses 76 to 79, wherein the first IP address is an address on a local area network designed to directly connect the first patient-side robotic procedure system to the robotic procedure console.

What is claimed is:

1. A robotic-assisted medical procedure system comprising:

a plurality of patient-side robotic procedure systems including a first patient-side robotic procedure system and a second patient-side robotic procedure system each comprising at least one of an instrument or an imaging system;

a plurality of robotic procedure consoles including a first robotic procedure console and a second robotic procedure console each configured to control a remotely located patient-side robotic procedure system of the plurality of patient-side robotic procedure systems; and a non-transitory computer readable medium storing instructions that, when executed by one or more processors, cause the one or more processors to:

provide a virtual network for connecting 1) the first robotic procedure console to the first patient-side robotic procedure system and 2) the second robotic procedure console to the second patient-side robotic procedure system, the virtual network utilizing a plurality of different and disparate physical networks that comprise a first physical network on which the first robotic procedure console is configured to reside, a second physical network on which the second robotic procedure console is configured to reside, a third physical network on which the first patient-side robotic procedure system is configured to reside, and a fourth physical network on which the second patient-side robotic procedure system is configured to reside;

authenticate the first and second robotic procedure consoles for the virtual network;

authenticate the first and second patient-side robotic procedure systems for the virtual network;

subsequent to authenticating the first robotic procedure console and the first patient-side robotic procedure system:

establish, over the virtual network, a first virtual network connection between the first robotic procedure console and the first patient-side robotic procedure system, the first virtual network connection utilizing the first physical network, the third physical network, and a backbone network; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system:

establish, over the virtual network, a second virtual network connection between the second robotic procedure console and the second patient-side robotic procedure system, the second virtual network connection utilizing the second physical network, the fourth physical network, and the backbone network; and transmit, over the second virtual network connection, data between the second robotic procedure console and the second patient-side robotic procedure system to permit the second robotic procedure console to remotely control the second patient-side robotic procedure system to perform a second medical procedure, the second medical procedure overlapping in time with the first medical procedure, wherein the first and second virtual network connections remain independent and separate despite sharing at least the backbone network.

2. The robotic-assisted medical procedure system of claim 1, wherein the first and second virtual network connections provide routing functionality.

3. The robotic-assisted medical procedure system of claim 2, wherein the plurality of patient-side robotic procedure systems further comprises a third patient-side robotic procedure system that is configured to reside on the first physical network on which the first robotic procedure console is configured to reside, and wherein the one or more processors are further caused to:

authenticate the third patient-side robotic procedure system for the virtual network; and subsequent to authenticating the first robotic procedure console and the third patient-side robotic procedure system:

establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

4. The robotic-assisted medical procedure system of claim 1, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

5. The robotic-assisted medical procedure system of claim 4, wherein the first IP address assigned to the first patient-side robotic procedure system is a first hard-coded IP address, and wherein the first hard-coded IP address of the first patient-side robotic procedure system overlaps with a hard-coded IP address of another patient-side robotic procedure system of the plurality of patient-side robotic procedure systems.

6. The robotic-assisted medical procedure system of claim 4, wherein the first IP address is an address on a local area network designed to directly connect the first patient-side robotic procedure system to the first robotic procedure console.

7. The robotic-assisted medical procedure system of claim 4, wherein:

the second robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks, wherein the second IP address is an address on a local area network designed to directly connect the second patient-side robotic procedure system to the second robotic procedure console.

8. A non-transitory computer readable medium storing instructions that, when executed by one or more processors, cause the one or more processors to:

provide a virtual network for connecting:

a first robotic procedure console of a plurality of robotic procedure consoles to a first patient-side robotic procedure system of a plurality of patient-side robotic procedure systems, the first patient-side robotic procedure system configured to be remotely located from the first robotic procedure console; and a second robotic procedure console of the plurality of robotic procedure consoles to a second patient-side robotic procedure system of the plurality of patient-side robotic procedure systems, the second patient-side robotic procedure system configured to be remotely located from the second robotic procedure console, the virtual network utilizing a plurality of different and disparate physical networks that comprise a first physical network on which the first robotic procedure console is configured to reside, a second physical network on which the second robotic procedure console is configured to reside, a third physical network on which the first patient-side robotic procedure system is configured to reside, and a fourth physical network on which the second patient-side robotic procedure system is configured to reside;

authenticate the first and second robotic procedure consoles for the virtual network;

authenticate the first and second patient-side robotic procedure systems for the virtual network;

subsequent to authenticating the first robotic procedure console and the first patient-side robotic procedure system:

establish, over the virtual network, a first virtual network connection between the first robotic procedure console and the first patient-side robotic procedure system, the first virtual network connection utilizing the first physical network, the third physical network, and a backbone network; and transmit, over the first virtual network connection, data between the first robotic procedure console and the first patient-side robotic procedure system to permit the first robotic procedure console to remotely control the first patient-side robotic procedure system to perform a first medical procedure; and subsequent to authenticating the second robotic procedure console and the second patient-side robotic procedure system:

establish, over the virtual network, a second virtual network connection between the second robotic procedure console and the second patient-side robotic procedure system, the second virtual network connection utilizing the second physical network, the fourth physical network, and the backbone network; and transmit, over the second virtual network connection, data between the second robotic procedure console and the second patient-side robotic procedure system to permit the second robotic procedure console to remotely control the second patient-side robotic procedure system to perform a second medical procedure, the second medical procedure overlapping in time with the first medical procedure, wherein the first and second virtual network connections remain independent and separate despite sharing at least the backbone network.

9. The non-transitory computer readable medium of claim 8, wherein the first and second virtual network connections provide routing functionality.

10. The non-transitory computer readable medium of claim 9, wherein the one or more processors are further caused to:

authenticate a third patient-side robotic procedure system for the virtual network, the third patient-side robotic procedure system configured to reside on the first physical network on which the first robotic procedure console is configured to reside; and subsequent to authenticating the first robotic procedure console and the third patient-side robotic procedure system:

establish, over the virtual network, a virtual interconnect between the first robotic procedure console and the third patient-side robotic procedure system, wherein the virtual interconnect provides switching functionality and does not provide routing functionality; and transmit, over the virtual interconnect, data between the first robotic procedure console and the third patient-side robotic procedure system to permit the first robotic procedure console to control the third patient-side robotic procedure system to perform a third medical procedure, wherein the third medical procedure does not overlap in time with the first medical procedure.

11. The non-transitory computer readable medium of claim 8, wherein the first robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

12. The non-transitory computer readable medium of claim 11, wherein the first IP address assigned to the first patient-side robotic procedure system is a first hard-coded IP address, and wherein the first hard-coded IP address of the first patient-side robotic procedure system overlaps with a hard-coded IP address of another patient-side robotic procedure system of the plurality of patient-side robotic procedure systems.

13. The non-transitory computer readable medium of claim 12, wherein the first IP address is an address on a local area network designed to directly connect the first patient-side robotic procedure system to the first robotic procedure console.

14. The non-transitory computer readable medium of claim 11, wherein:

the second robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks, wherein the second IP address is an address on a local area network designed to directly connect the second patient-side robotic procedure system to the second robotic procedure console.

15. A robotic-assisted medical procedure system comprising:

a plurality of patient-side robotic procedure systems including a first patient-side robotic procedure system and a second patient-side robotic procedure system each comprising at least one of an instrument or an imaging system;

a robotic procedure console configured to control the plurality of patient-side robotic procedure systems located remotely from the robotic procedure console; and a non-transitory computer readable medium storing instructions that, when executed by one or more processors, cause the one or more processors to:

provide a virtual network for connecting the robotic procedure console to the first and second patient-side robotic procedure systems, the virtual network utilizing a plurality of different and disparate physical networks that comprise a first physical network on which the robotic procedure console is configured to reside and a second physical network on which the first and second patient-side robotic procedure systems are configured to reside;

authenticate the robotic procedure console for the virtual network;

authenticate the first and second patient-side robotic procedure systems for the virtual network;

subsequent to authenticating the robotic procedure console and at least the first patient-side robotic procedure system:

establish, over the virtual network, a first virtual network connection between the robotic procedure console and the first patient-side robotic procedure system;

transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure; and subsequent to completion of the first medical procedure:

establish, over the virtual network, a second virtual network connection between the robotic procedure console and the second patient-side robotic procedure system;

transmit, over the second virtual network connection, data between the robotic procedure console and the second patient-side robotic procedure system to permit the robotic procedure console to remotely control the second patient-side robotic procedure system to perform a second medical procedure; and terminate the second virtual network connection subsequent to completion of the second medical procedure, wherein each of the first and second virtual network connections remain independent and separate from any other temporally overlapping virtual network connection that shares at least one physical network with the first or second virtual network connection.

16. The robotic-assisted medical procedure system of claim 15, wherein the first and second virtual network connections provide routing functionality.

17. The robotic-assisted medical procedure system of claim 16, wherein the plurality of patient-side robotic procedure systems further comprises a third patient-side robotic procedure system that is configured to reside on the first physical network on which the robotic procedure console is configured to reside, and wherein the one or more processors are further caused to:

authenticate the third patient-side robotic procedure system for the virtual network; and subsequent to authenticating the robotic procedure console and the third patient-side robotic procedure system:

establish, over the virtual network, a virtual interconnect between the robotic procedure console and the third patient-side robotic procedure system, wherein the virtual interconnect provides switching functionality and does not provide routing functionality;

transmit, over the virtual interconnect, data between the robotic procedure console and the third patient-side robotic procedure system to permit the robotic procedure console to control the third patient-side robotic procedure system to perform a third medical procedure, wherein the third medical procedure does not overlap in time with the first or second medical procedure; and terminate the virtual interconnect subsequent to completion of the third medical procedure.

18. The robotic-assisted medical procedure system of claim 15, wherein the robotic procedure console utilizes a first IP address assigned to the first patient-side robotic procedure system to communicate with the first patient-side robotic procedure system, and wherein the first IP address is automatically encapsulated to facilitate communication with the first patient-side robotic procedure system over the first virtual network connection that traverses multiple local area networks.

19. The robotic-assisted medical procedure system of claim 18, wherein the first IP address assigned to the first patient-side robotic procedure system is a first hard-coded IP address, and wherein the first hard-coded IP address of the first patient-side robotic procedure system overlaps with a hard-coded IP address of another patient-side robotic procedure system of the plurality of patient-side robotic procedure systems.

20. The robotic-assisted medical procedure system of claim 18, wherein the first IP address is an address on a local area network designed to directly connect the first patient-side robotic procedure system to the robotic procedure console.

21. The robotic-assisted medical procedure system of claim 18, wherein:

the robotic procedure console utilizes a second IP address assigned to the second patient-side robotic procedure system to communicate with the second patient-side robotic procedure system; and the second IP address is automatically encapsulated to facilitate communication with the second patient-side robotic procedure system over the second virtual network connection that traverses multiple local area networks, wherein the second IP address is an address on a local area network designed to directly connect the second patient-side robotic procedure system to the robotic procedure console.

22. The robotic-assisted medical procedure system of claim 15, further comprising another robotic procedure console configured to be connected to the first patient-side robotic procedure system by one or more dedicated cables or a direct local area network (LAN) connection and a switching circuitry configured to be integrated with the first patient-side robotic procedure system, the switching circuitry further configured to:

cause the first patient-side robotic procedure system to operate in a first mode in which the first patient-side robotic procedure system and the another robotic procedure console connected to the first patient-side robotic procedure system by one or more dedicated cables or a direct local area network (LAN) connection exchange data to permit the another robotic procedure console to control the first patient-side robotic procedure system to perform the first medical procedure; and cause the first patient-side robotic procedure system to operate in a second mode in which the first patient-side robotic procedure system and the robotic procedure console exchange data to permit the robotic procedure console to remotely control the first patient-side robotic procedure system to perform the first medical procedure;

responsive to a first signal, cause the first patient-side robotic procedure system to transition from operating in the first mode to operating in the second mode; and responsive to a second signal, cause the first patient-side robotic procedure system to transition from operating in the second mode to operating in the first mode.

23. A non-transitory computer readable medium storing instructions that, when executed by one or more processors, cause the one or more processors to:

provide a virtual network for connecting a robotic procedure console to first and second patient-side robotic procedure systems of a plurality of patient-side robotic procedure systems, the virtual network utilizing a plurality of different and disparate physical networks that comprise a first physical network on which the robotic procedure console is configured to reside and a second physical network on which the first and second patient-side robotic procedure systems are configured to reside;

authenticate the robotic procedure console for the virtual network;

authenticate the first and second patient-side robotic procedure systems for the virtual network;

subsequent to authenticating the robotic procedure console and at least the first patient-side robotic procedure system:

establish, over the virtual network, a first virtual network connection between the robotic procedure console and the first patient-side robotic procedure system;

transmit, over the first virtual network connection, data between the robotic procedure console and the first patient-side robotic procedure system to permit the robotic procedure console to remotely control the first patient-side robotic procedure system to perform a first medical procedure; and terminate the first virtual network connection subsequent to completion of the first medical procedure; and subsequent to completion of the first medical procedure:

establish, over the virtual network, a second virtual network connection between the robotic procedure console and the second patient-side robotic procedure system;

transmit, over the second virtual network connection, data between the robotic procedure console and the second patient-side robotic procedure system to permit the robotic procedure console to remotely control the second patient-side robotic procedure system to perform a second medical procedure; and terminate the second virtual network connection subsequent to completion of the second medical procedure, wherein each of the first and second virtual network connections remain independent and separate from any other temporally overlapping virtual network connection that shares at least one physical network with the first or second virtual network connection.

* * * * *